(12) United States Patent
Rant et al.

(10) Patent No.: US 9,885,687 B2
(45) Date of Patent: Feb. 6, 2018

(54) APPARATUS AND METHOD FOR EVALUATING CHARACTERISTICS OF TARGET MOLECULES

(71) Applicant: Dynamic Biosensors GmbH, Martinsried/Planegg (DE)

(72) Inventors: Ulrich Rant, Munich (DE); Wolfgang Kaiser, Munich (DE); Paul Andreas Hampel, Fischbachau (DE); Jens Niemax, Munich (DE); Andreas Langer, Munich (DE); Jelena Knezevic, Munich (DE)

(73) Assignee: Dynamic Biosensors GmbH, Martinsried/Planegg (DE)

( * ) Notice: Subject to any disclaimer, the term of this patent is extended or adjusted under 35 U.S.C. 154(b) by 0 days.

(21) Appl. No.: 14/856,852

(22) Filed: Sep. 17, 2015

(65) Prior Publication Data
US 2016/0011148 A1    Jan. 14, 2016

Related U.S. Application Data

(60) Division of application No. 13/850,930, filed on Mar. 26, 2013, now Pat. No. 9,164,055, which is a
(Continued)

(30) Foreign Application Priority Data

Sep. 27, 2010    (EP) .................................... 10180282

(51) Int. Cl.
*G01N 27/447*    (2006.01)
*C12Q 1/68*    (2006.01)
(Continued)

(52) U.S. Cl.
CPC ..... *G01N 27/44726* (2013.01); *C12Q 1/6825* (2013.01); *G01N 21/6408* (2013.01);
(Continued)

(58) Field of Classification Search
CPC ....... G01N 27/44726; G01N 27/44756; G01N 27/327; G01N 33/5438; G01N 21/6458;
(Continued)

(56) References Cited

U.S. PATENT DOCUMENTS

| 6,001,266 A | 12/1999 | Bier | 209/127.1 |
|---|---|---|---|
| 2004/0072232 A1 | 4/2004 | Gulati | 435/6.17 |

(Continued)

FOREIGN PATENT DOCUMENTS

| EP | 2192401 A1 * | 6/2010 | B82Y 15/00 |
|---|---|---|---|
| JP | 2004028798 | 1/2004 | |

OTHER PUBLICATIONS

Rant et al., "Dissimilar kinetic behavior of electrically manipulated single- and double-stranded DNA tethered to a gold surface," Biophysical Journal, vol. 90, No. 10, May 2006, pp. 3666-3671.
(Continued)

*Primary Examiner* — J. Christopher Ball
(74) *Attorney, Agent, or Firm* — Sunstein Kann Murphy & Timbers LLP

(57) ABSTRACT

Arrangements are described for evaluating characteristics of target molecules. A biochip is received which includes a substrate to which charged probe molecules are attached. The probe molecules have a marker to allow generating signals indicative of the distance of a portion of the probe molecule from the substrate. The signals are detected and means for an external electric field is generated to which the probe molecules are exposed. A control means acts to: (A) apply an external electric field causing the portion of the probe molecule to approach the substrate, and (B) apply an external electric field causing the portion of the probe molecule to move away from the substrate. The signal is recorded as a function of time during step (A) and/or step
(Continued)

(B). Steps (A) and (B) are repeated for a predetermined number of times and the recorded signals are combined.

14 Claims, 17 Drawing Sheets

Related U.S. Application Data continuation of application No. PCT/EP2011/004833, filed on Sep. 27, 2011.

(51) Int. Cl.
*G01N 21/64* (2006.01)
*G01N 33/543* (2006.01)
*G01N 27/327* (2006.01)

(52) U.S. Cl.
CPC ....... *G01N 21/6458* (2013.01); *G01N 27/327* (2013.01); *G01N 27/44756* (2013.01); *G01N 33/5438* (2013.01); *C12Q 1/6823* (2013.01); *G01N 2021/6432* (2013.01)

(58) Field of Classification Search
CPC ....... G01N 21/6408; G01N 2021/6432; C12Q 1/6825; C12Q 1/6823
See application file for complete search history.

(56) References Cited

U.S. PATENT DOCUMENTS

2005/0069932 A1    3/2005  Arinaga ................. 435/6.12
2010/0133121 A1    6/2010  Arinaga ................. 205/787

OTHER PUBLICATIONS

Sendner et al., "Dynamics of end grafted 1-15 DNA molecules and possible biosensor applications," Physica Status Solidi. A: Applied Research, Wiley-Vch Verlag, Berlin, DE, vol. 203, No. 14, Nov. 10, 2006, pp. 3476-3491.
Rant et al., "Dynamic electrical switching of DNA layers on a metal surface," Nano Letters, ACS, Washington, DC, vol. 4, No. 12, Dec. 1, 2004, pp. 2441-2445.
Takeishi et al., "Observation of electrostatically released DNA from gold electrodes with controlled threshold voltages." *The Journal of chemical physics* 120.12 (2004): 5501-5504.
Rant et al., "Excessive counterion condensation on immobilized ssDNA in solutions of high ionic strength." *Biophysical journal* 85.6 (2003): 3858-3864.
Rant, Ulrich, Declaration Under 37 C.F.R. § 1.132.
ISA/European Patent Office, International Search Report and Written Opinion for PCT/EP2011/004833 dated Nov. 22, 2011.

\* cited by examiner

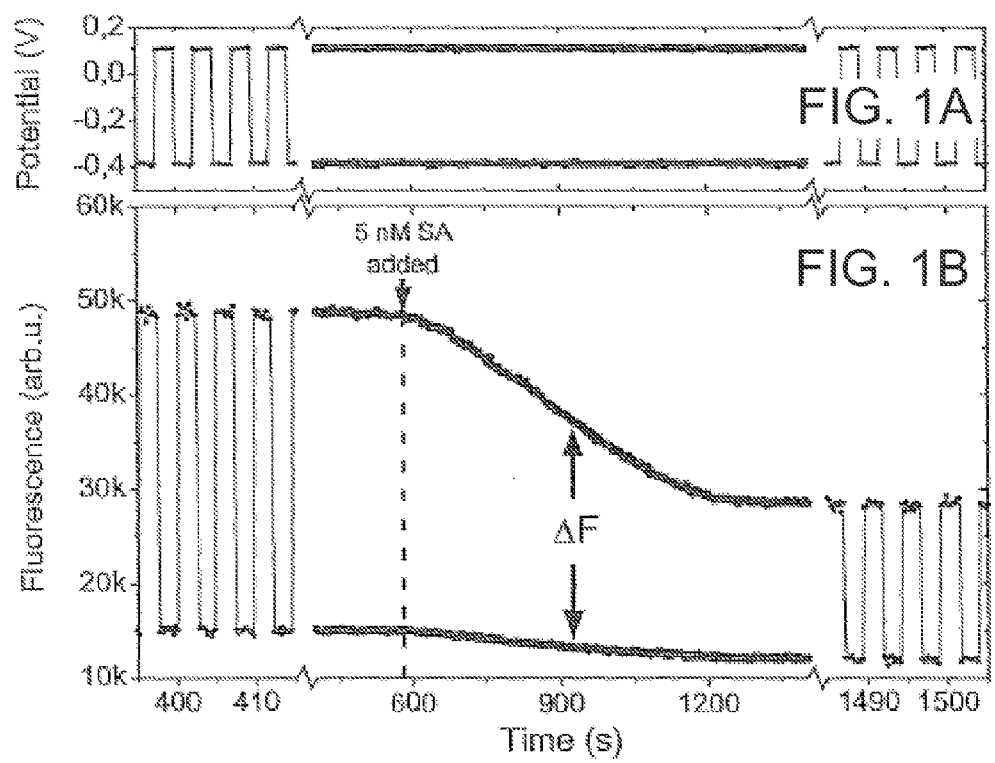
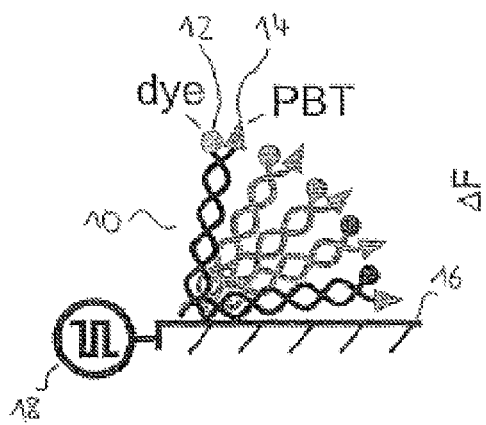
FIG. 1C
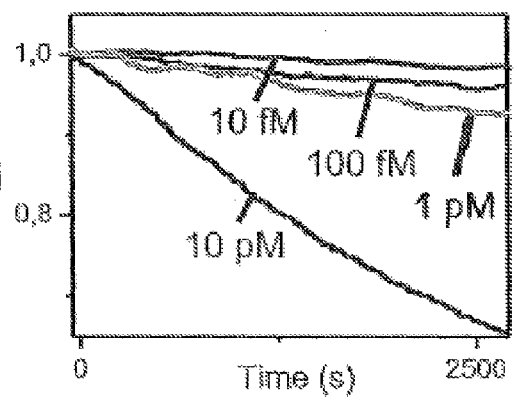
FIG. 1D

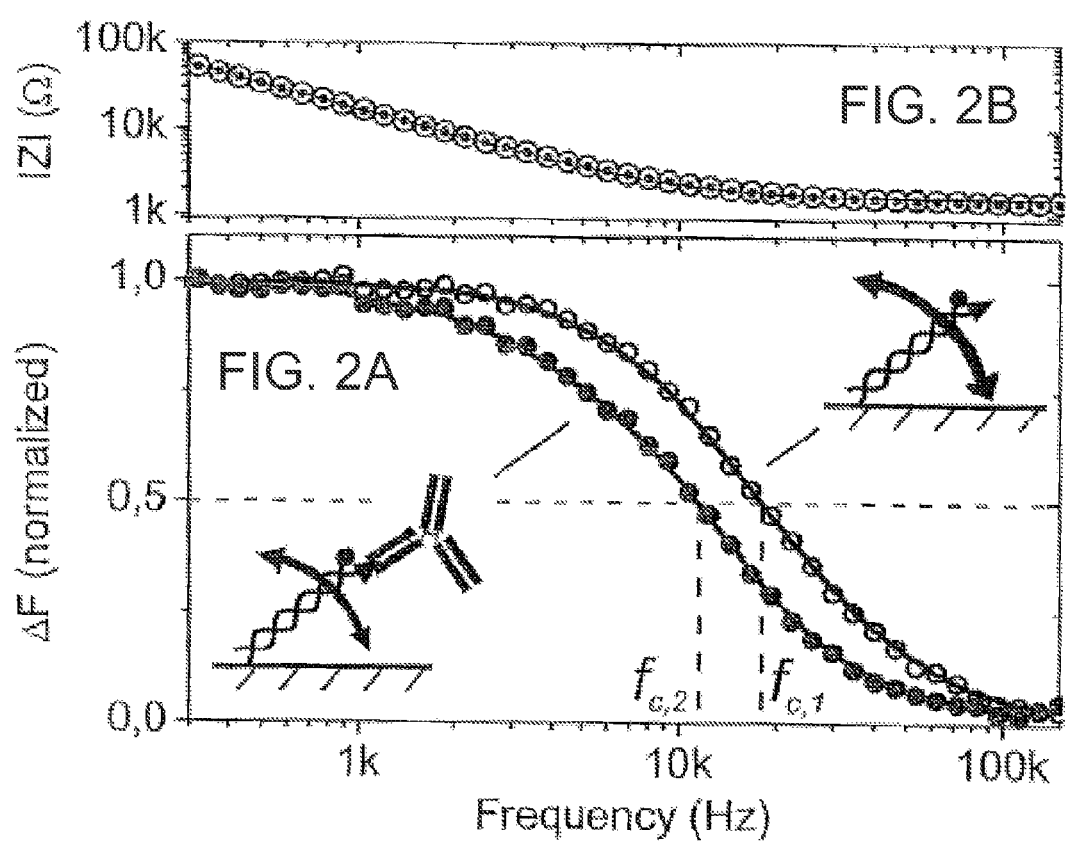

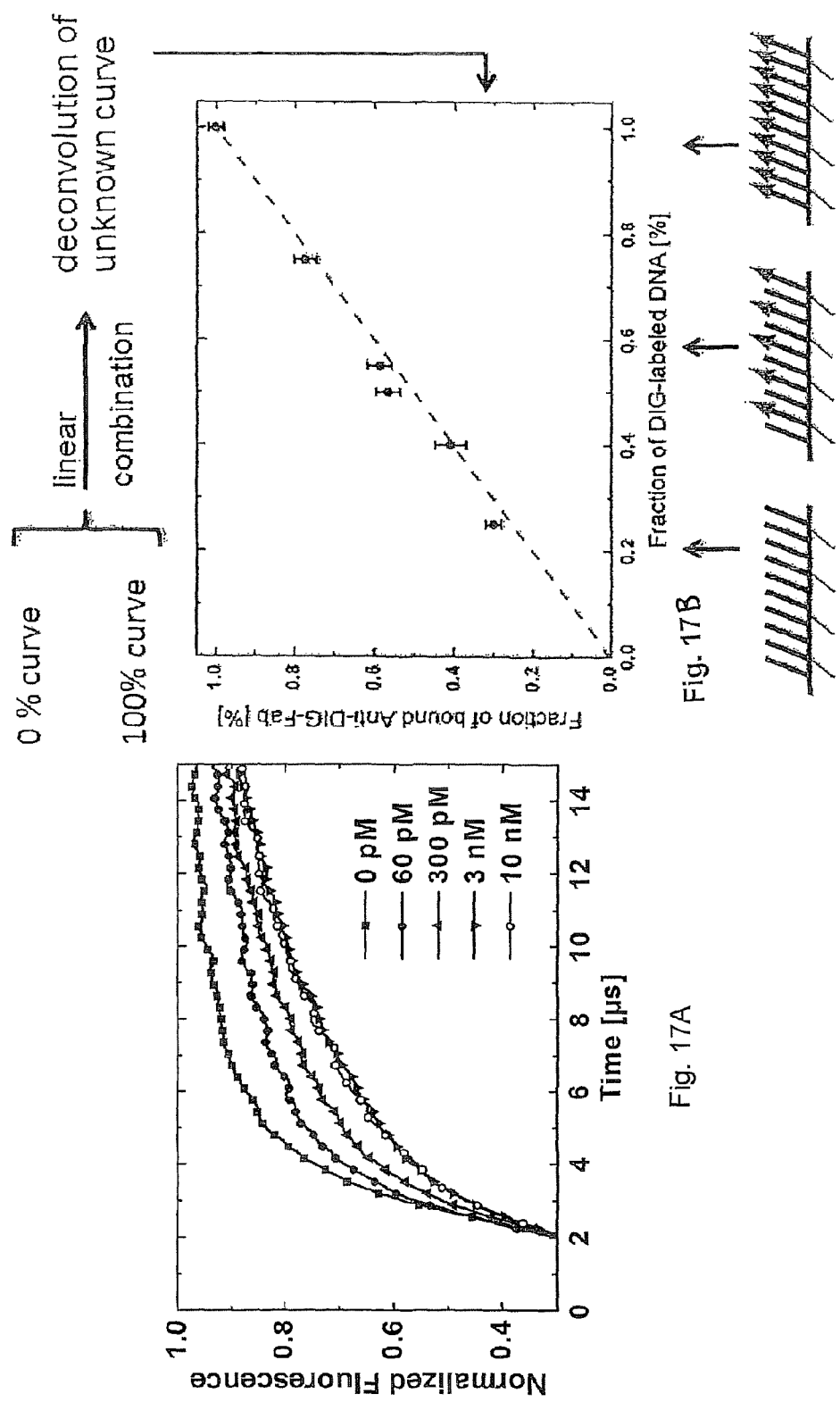

| protein | $k_{on}$ ($10^5$ M$^{-1}$s$^{-1}$) | $k_{off}$ in 10 mM imidazole ($10^{-3}$ s$^{-1}$) |
| --- | --- | --- |
| A | 4.6 ± 0.5 | 7.4 ± 0.8 |
| G | 5.3 ± 0.5 | 5.8 ± 0.5 |
| L | 1.6 ± 0.2 | 4.9 ± 0.6 |
| INFα | 0.4 ± 0.1 | 13 ± 2 |
| MOG | 3.1 ± 0.4 | 22 ± 5 |
| Fab | 26 ± 11 | 2.9 ± 0.4 |

APPARATUS AND METHOD FOR EVALUATING CHARACTERISTICS OF TARGET MOLECULES

CROSS-REFERENCE TO RELATED APPLICATIONS

This application is a divisional of U.S. patent application Ser. No. 13/850,930, filed Mar. 26, 2013, which is a continuation of Patent Cooperation Treaty Application PCT/EP2011/004833, filed Sep. 27, 2011, which in turn claimed priority from European Patent Application 10180282.5, filed Sep. 27, 2010; each of which is incorporated herein by reference in its entirety.

FIELD OF THE INVENTION

The present invention relates to the field of nanobiotechnology. More particularly, the present invention relates to a surface-based molecular dynamics measurement concept that has been recently introduced by the present inventors.

BACKGROUND OF THE INVENTION AND RELATED PRIOR ART

In the field of nanobiotechnology, particular attention has been focussed on biochips, such as DNA chips and protein chips as an effective means for simplifying nucleic acid and protein testing in areas such as clinical diagnosis and drug development. Biochips, which are often also referred to as micro arrays, are substrates formed from glass, silicon, plastic, metal or the like on which multiple differing probes composed of bio molecules such as DNA and proteins are placed as spots in high-density areas. Binding of target molecules with probe molecules is traditionally detected by means of a fluorescence label or the like associated with the target molecules.

The present inventors have recently introduced a chip-compatible scheme for the label-free detection of bio molecules by a surface-based molecular dynamics measurement, which the inventors termed "switchSENSE method" for reasons that will become apparent below. In this method, the probe molecule is a charged molecule, particularly a charged polymer or a charged nanowire, that has a first portion attached to a substrate. The probe molecule has a marker allowing to generate signals indicative of the distance of a second portion, e.g. the distal end of the probe molecule from the substrate. The probe molecule further has a capture part capable of binding with certain target molecules that are to be detected.

In the switchSENSE method, the probe molecule is subjected to an external AC field. Since the probe molecule is charged, depending on the current polarity of the external field, said second portion of the probe molecule which is not directly attached to the substrate will approach or move away from the substrate. The change of configuration can be thought of as a switching between a "standing" configuration, in which the second portion is maximally removed from the substrate, and a "lying" configuration, in which the second portion is closest to the substrate. However, since the probe molecule is not limited to any specific shape, this terminology is rather metaphorical and should not be understood to impose any restriction on the type or shape of the probe molecule used.

By analyzing the switching behaviour between the standing and lying configurations, it is possible to detect the presence of a target molecule bound to the probe molecule. Importantly, for this detection it is not necessary that the target molecule itself is labelled in any sense, which is why the switchSENSE method is referred to as a "label-free detection method".

For a better illustration of the switchSENSE method, reference is made to FIGS. 1 to 3, which have been taken from Ulrich Rant et. al., "Detection and Size Analysis of Proteins with Switchable DNA Layers", Nano Letters 2009, Vol. 9, Nr. 4, 1290-1295 (prior art document 1) co-authored by some of the present inventors, which is included into the present disclosure by reference. It is to be understood that reference to this work is only meant to explain the relevant prior art but is not intended to limit the invention in any way.

In prior art document 1, (negatively charged) DNA molecules were used as probe molecules. In particular, synthetic 72-mer oligonucleotides were modified with a thiol (HS) to covalently tether the strands to the substrate, which was a gold surface in this prior art. The distal end of the DNA molecule was labelled with a fluorescent marker (cyanine die, Cy3). The single-stranded (ss) HS-ss DNA-Cy3 sequence was hybridized with a complementary strand that was modified with a protein binding tag (PBT), so that a double-stranded capture probe was formed.

The DNA layer thus formed was activated by an external electric field. Alternating potentials were applied in aqueous salt solution between the gold surface, acting as a work electrode, and a counter electrode. The applied bias polarizes the electrode interface, leading to the formation of Gouy-Chapman-Stern screening layer on the solution side. The resulting electric field was confined to the electrode proximity, with an extension of only a few nanometers, but was very intense with a field strength of up to 100 kV/cm even for low bias potentials of less than 1 V. Since the DNA is intrinsically negatively charged along its deprotonized phosphate backbone, the molecules align in the electric field and the DNA conformation can be switched between the abovementioned "standing" and "lying" state, depending on the polarity of the applied bias.

The switching action can be monitored by observing the fluorescence from the Cy3 fluorescence labels attached to the DNAs' upper ends. A non-radiative energy transfer from the optically excited dye to surface plasmons in the gold electrode quenches the emitted fluorescence intensity when the fluorescence marker, i.e. the upper DNA end, approaches the surface. Accordingly, the fluorescence marker is an example of a marker allowing to generate signals indicative of the distance of a second portion of the probe molecules (i.e. in this example, the distal ends) from the substrate, i.e. the gold surface.

In FIG. 1C, the probe molecule 10 used in prior art document 1 is schematically shown. As mentioned above, the probe molecule 10 is a double-stranded DNA, having a fluorescence marker (dye) 12 and a protein binding tag 14 attached to its distal end. Further, the gold substrate 16 and a voltage source 18 for biasing the gold surface 16 are schematically shown. If a negative voltage is applied to the gold surface or work electrode 16, the probe molecule 10 is repelled and pushed to the standing configuration schematically shown in FIG. 1C. Conversely, if a positive voltage is applied to the gold substrate 16, the distal end of probe molecule 10 approaches the same, i.e. the probe molecule 10 acquires the lying configuration. As is schematically indicated in FIG. 1C, due to the stiffness of the molecule, the switching between the standing and lying configurations is thought of as a rotation of the DNA around its fixed end.

With reference to FIGS. 1A-1D, and specifically FIG. 1B, the switching between the standing and lying configurations can be detected by observing the fluorescence light emitted by the marker 12. If the probe molecule 12 is in the standing configuration, the distance between the fluorescence marker 12 and the gold electrode 16 is the largest, and the fluorescence emission is not quenched. Accordingly, in this standing configuration, the detected fluorescence is the largest. Conversely, if the distal end of probe molecule 10 and hence the fluorescence marker 12 approaches the gold electrode 16, the aforementioned non-radiative energy transfer from the optically excited fluorescence marker 12 to surface plasmons in the gold electrode 16 quenches the emitted fluorescence intensity and thus leads to a decreased fluorescence intensity, see FIG. 1B. Herein, the difference in fluorescence intensity between the standing and lying configurations is referred to as "ΔF".

As is demonstrated in the above-referenced prior art document 1, it is shown that binding of target molecules (proteins in the specific example) to the probe molecule 10 alters the attainable switching amplitude of the probe molecule layer, which is most likely caused by inducing steric interactions between neighbouring molecules. This phenomenon can be observed in FIG. 1B, where at the time 600 s, unlabelled streptavidin (SA) is added to the fluid environment and binds to the protein binding tag 14. As more and more of the SA binds with the probe molecule 10, ΔF decreases, until it reaches a plateau at approximately 1200 s. Accordingly, the modulation of ΔF serves as an indicator that a target molecule (in this case SA) has bound to the protein binding tag 14 of the probe molecule 10. Further, by observing the dynamic behaviour of ΔF, also the binding kinetics can be determined, in particular a binding or dissociation rate between the target and probe molecules, an affinity constant and a dissociation constant.

As is further demonstrated in prior art document 1, this label-free detection of a target molecules binding to the probe molecules via ΔF is extremely sensitive, with a detection limit below 100 fmol/l.

Further, the inventors of the present invention have shown that it is possible to discern information about the size of the target molecule by analyzing the frequency response of the switching dynamics, as will be explained with reference to FIG. 2 A-B taken from prior art document 1 as well. In FIG. 2A, the normalized switching amplitude ΔF as a function of biasing voltage frequency is shown for the pristine probe DNA in the upper curve and after binding of the immunoglobulin G (IgG) antibody of a sheep (lower curve). As a switching field, a sinusoidal ac bias voltage is applied to the work electrode, the frequency of which is varied. In FIG. 2A, the resulting frequency spectra are shown, which each comprise three distinct regimes:
(i) for low frequencies (<1 kHz), the DNA molecules follow the electrical excitation with maximal efficiency, leading to maximum oscillation of the probe molecule 10 and hence a maximum value of ΔF;
(ii) in an intermediate regime, the switching amplitude ΔF decays; and
(iii) in a high frequency region (>100 kHz), the probe molecule 10 cannot be driven by the applied AC potential anymore and hence ΔF vanishes.

The frequency range (ii) is of particular interest because it reflects the finite time constant of the switching process. To compare the switching dynamics of different samples, the frequency at which the amplitude ΔF has decreased to 50% of its initial value is evaluated. The frequency is called "cut-off frequency $f_c$" in the following. As can be seen from FIG. 2, for the pristine DNA layer a cut-off frequency $f_{c,1}$=18 kHz is found. After IgG (sheep) is bound to the DNA layer, one observes a pronounced decrease of the cut-off frequency, namely $f_{c,2}$=11.5 kHz. Accordingly, it is seen that the binding of target molecules to the probe molecules slows down the dynamics of the switching process down.

It is believed that the slowing down of the switching process is caused by the increased hydrodynamic drag due to the attached target molecule. It is further believed that the increment in molecular weight does not play an as important role, since the DNA motion is extremely over-damped, so that inertial effects can be neglected. As has been shown by the inventors of the present invention, the frequency shift induced by target molecules can be used to determine the target molecules' size, in particular their effective Stokes radius. With regard to the example of FIG. 2, the inventors have measured frequency shifts for various antibodies and antibody fragments. FIGS. 3A and 3B summarize cut-off frequency measurements for proteins of varying size. The normalized cut-off frequency is plotted versus the normal molecular weight in panel A (Fab sheep (50 kDa), streptavidin (75 kDa), Fab2, goat (100 kDa), IgG sheep (150 kDa) and IgG goat (160 kDa)). The cut-off frequency versus the respective hydrodynamic diameters Dh are shown in panel B. FIG. 3C shows the $D_h$ distribution measured by dynamic light scattering, see prior art document 1 for more details.

As can be seen from FIG. 3, a monotonous decrease of the normalized cut-off frequency is found for increasing size of the bound protein. In particular, Fab and Fab2 fragments can be clearly discriminated from uncleaved antibodies. Accordingly, measuring the frequency response of the fluorescence amplitude, the size of the target molecules can be evaluated with remarkable precision.

As is obvious from the above, using the switchSENSE method, both the binding of the target molecule as such as well as the size of the target molecules can be evaluated for unlabelled targets. In particular, the evaluation of target molecule size by analyzing the frequency response has proven to be a very powerful tool that requires only limited experimental effort and proved to be very robust. The frequency response analysis is also the subject of further publications and patent applications co-authored by some of the present inventors, see in particular U. Rant et. al, "Switchable DNA Interfaces for the Highly Sensitive Detection of Label-free DNA Targets", PNAS (270), Vol. 104, Nr. 44, p. 17364-17369, EP 2 192 401 A1 and US 2005/0069932 A1.

While the combined detection and size evaluation of target molecules according to the above prior art has proven to be very successful, there is an on-going desire to increase the precision and reliability of the evaluation of characteristics of the target molecules. A further object of the invention is to provide a method for evaluating characteristics of a target molecule that would be particularly suitable for implementing in commercially available apparatuses, thus lifting the switchSENSE technology from a scientific concept to a practical tool that can be routinely used not only in academic research but also in pharma and biotech industry as well as laboratories for clinical diagnostics and hospitals. A further problem underlying the invention is to provide an apparatus that would allow evaluating characteristics of a target molecule bound to a probe molecule with good precision, yielding reliable and trustworthy results to routine users who cannot be expected to question the analysis results but instead need to rely on them.

SUMMARY OF THE INVENTION

The above objects are met by an apparatus for evaluating one or more characteristics of target molecules according to claim 1 and by a method according to claim 8. Advantageous further developments are defined in the dependent claims.

According to a first aspect of the invention, an apparatus for evaluating one or more characteristics of target molecules is provided. The apparatus of the invention comprises means for receiving a biochip, wherein the biochip comprises a substrate to which probe molecules are attached with a first portion thereof. The probe molecules are charged and have a marker for allowing to generate signals indicative of the distance of a second portion of the probe molecule from the substrate. Herein, the substrate may be a work electrode and the marker could be a fluorescence marker as in the prior art described above, but the invention is not limited to this.

Further, the apparatus of the invention comprises means for detecting the signal generated with the marker and means for a generating an external electric field which the probe molecules are exposed to when the biochip is received in the receiving means. Also, the apparatus of the invention comprises a control means configured to control the electric field generating means to (A) apply an external electric field causing the second portion of the probe molecule to approach the substrate when the biochip is received in the receiving means, and
(B) apply an external electric field causing the second portion of the probe molecule to move away from the substrate.

Herein, the control means is further configured to control the signal detecting means to record the signal indicative of the distance of the second portion from the substrate as a function of time during step (A) and/or step (B). The control means is further configured to control the electric field generation means and the detecting means such as to repeat steps (A) and (B) for a predetermined number of times and is configured to combine the recorded signals such as to generate an averaged time-resolved signal indicative of the process of the second part of the probe molecule approaching and/or moving away from the substrate.

Finally, the apparatus comprises an analysis module for analyzing and/or processing said combined signal such as to determine said one or more characteristics of said target molecule, and preferable an output device for outputting the at least one or more characteristics of said target molecule. Alternatively, the apparatus may comprise an interface allowing to couple the apparatus directly or indirectly with an output device such as a display.

Unlike the prior art discussed above, the apparatus of the invention dispenses with the above concept of determining the size or effective Stokes radius of the target molecules by the frequency response of the switching amplitude $\Delta F$. Instead, the apparatus of the invention carries out a time-resolved measurement of the switching process itself, i.e. of the transition between the standing configuration and the lying configuration and vice versa.

In spite of the indisputable success of the characterization via frequency response, the inventors have found out that the reliability of the evaluation of target characteristics can be improved by replacing the frequency response measurement, which conceptually is a spectral approach, by a time-resolved measurement. In fact, the inventors have found out that while the frequency response measurement in some scenarios is very sensitive when it comes to evaluating the size of target molecules, in other scenarios it will fail to distinguish target molecules of different sizes, which can however be distinguished with the apparatus and method of the invention based on a time-resolved measurement of the switching process itself. From the inventors' point of view, who have developed and explored the frequency response method themselves, this is a surprising and unforeseeable result.

It should be noted that one of the inventors had presented time-resolved fluorescence measurements of single- and double-stranded DNA tethered to a gold surface in an earlier publication (see U. Rant et al., "Dissimilar Kinetic Behaviour of Electrically Manipulated Single- and Double-Stranded DNA Tethered to a Gold Surface", Biophysical Journal, Vol. 90 (2006), p. 3666-3671). However, this time-resolved measurement was only related to the DNA as such, not to a DNA functionalized as a probe molecule, and in particular not a probe molecule to which a target molecule was or could have been bound. In other words, this prior work was not related to the characterization of target molecules.

What is more, the experience the inventor gained with this prior work would not at all have suggested to employ a time-dependent measurement of the switching process for evaluating characteristics of target molecules bound to probe molecules. Namely, using the box car measurement approach in this prior work, recording a single time-resolved measurement of one switching cycle took several days, which is of course prohibitive for any application in target analysis, where results are needed quickly and where the targets will only bind to the probe molecule for a limited time. Surprisingly, however, the inventors could confirm that it was nevertheless possible to carry out the time-resolved measurement of the switching process at a speed and with a robustness comparable with that of the frequency response method described above.

While best analysis results can be obtained when recording the signals during both steps (A) and (B) it is nevertheless possible to base the analysis on the signals of one of the steps only. This is particularly true for step (B), as experiments by the inventors have confirmed that valuable information about the bound target molecules can be discerned from a time-resolved analysis of the rising process of the probe molecule.

According to the first aspect of the invention, the apparatus further comprises an analysis module for automatically analyzing and/or processing the combined signal such as to determine the one or more characteristics of the target molecule. By integrating such analysis module with the apparatus, the information of interest to the user of the apparatus can be provided rather than the experimental data itself, and this information or analysis result can preferably be presented to the user by the output device.

In a preferred embodiment, the analysis module is configured to analyze and/or process the combined signals such as to determine a time delay between
1. switching the external field between steps (A) and (B) and
2. the time-dependent signal reaching a predetermined threshold value.

Herein, the predetermined threshold value may for example correspond to a predetermined percentage of the maximum of the combined value. In this embodiment, the analysis thus yields only two numeric values that can be correlated with the size or effective Stokes radius of the target molecule bound to the probe molecule.

Note that even in this simple embodiment, the apparatus of the invention yields more information than the frequency response method as described above, which only yields a single numeric value—the cut-off frequency—reflecting both the dynamics of the transition from standing to lying (down transition) and from lying to standing (up transition).

At first sight one would assume that not much insight could be gained by this additional information. After all, one would assume that the hydrostatic drag of the target molecule would have a similar effect during up and down transitions, thus retarding both processes in a similar way. This is true in some scenarios, and this is why the frequency response method proved so successful in many cases. However, the inventors have observed that there are also scenarios in which the target molecule influences the up and down transitions in a dissimilar way. In particular, while of course the hydrostatic drag will always play a role in the switching dynamics, in some cases it may not play the only and not even the decisive role. Instead, the inventors have observed that especially for the down transition, the dynamics also has a stochastic component, which presumably has to do with the electric field being confined to the electrode proximity due to the Gouy-Chapman-Stern screening layer. It is believed that the probe molecule needs to fluctuate due to Brownian motion to a "starting configuration" before the external electric field can effectively initiate the down transition. Accordingly, there is a time component to the down transition unrelated or at least not directly related to the hydrodynamic resistance. Since the cut-off frequency determined with the frequency response method always reflects a combination of up and down transition time constants, the time constant of the down transition may dominate the result to an extent that smaller differences in the effective Stokes radius may remain unobserved. This will be demonstrated below with reference to an actual example.

In addition or alternatively, the analysis module may be configured to analyze and/or process the combined signals such as to determine the time-derivative thereof. In particular, it is possible to determine only the maximum time derivative of the combined signal, which would as well only give a single number for the up and down transitions, respectively. However, it is believed that this number is more closely and directly correlated with the effective Stokes radius than e.g. the cut-off frequency of the frequency response measurement. In particular, it is believed that the maximum signal derivative is largely unrelated to the stochastic delay of the transition due to Brownian motion, as it reflects the maximum speed of the transition, which is presumably governed by the effective Stokes radius.

In addition or alternatively, the analysis module may be configured to compare the combined signal with empirical data or model data obtained from an analytical model or a simulation. Experiments of the inventors have shown that the time-resolved signals bear additional information that cannot be summarized in a single number. Instead, it appears that the signal versus time graphs for different targets have peculiar shapes and characteristic features that can be employed to identify targets with more precision, for instance, with respect to the target molecule shape or conformational flexibility. For example, it has been observed that the graph of the signal versus time for some targets displays some characteristic kinks, while for other targets it is entirely smooth. Even if this behaviour is not entirely understood yet, this observation can already be used to compare the recorded signal with empirically known targets and to detect a match. This comparison can be automated and integrated into the analysis module.

Further, the inventors have also elaborated analytical models predicting the signal to be expected for target molecules. An article "Analytical Model Describing the Molecular Dynamics of DNA-Protein Conjugates Tethered to Electrified Surfaces" by Andreas Langer, Wolfgang Kaiser and Ulrich Rant will be submitted for publication shortly after filing of the present application. In this work, an analytical model describing the switching behaviour of short double-stranded DNA molecules is elaborated, and model parameters are discerned from experimental data. After such a model is established, the time-resolved signal to be expected for any given target size can be calculated, and the result of this calculation can be compared with the combined signal obtained with the apparatus. This way it can for example be confirmed whether the experimental data and the effective Stokes radius discerned therefrom is consistent with the model or not. Accordingly, the analysis module may output a reliability value together with the outputted characteristic of the target molecule.

The inventors have noticed that the switching process of the probe molecule is a stochastic process that is governed by Brownian motion type effects plus a drift due to the external electric field. More specifically, it has been found that the switching dynamics can be described very realistically based on a probability distribution $p(\vec{x}, t)$ defining the probability that the probe molecule acquires a configuration $\vec{x}$ at a time t in a time-dependent external field. In this model, the Stokes radius or size of the target molecule is accounted for by a drift and/or a diffusion of the probability with regard to $\vec{x}$. Herein, $\vec{x}$ can be any one- or more-dimensional coordinate that can parameterize the configuration of the probe molecule. The inventors have found that for a suitably stiff probe molecule, such as double-stranded DNA, the configuration can be sufficiently parameterized by the angle $\alpha$ of the probe molecule with regard to the substrate.

In a preferred embodiment, the analysis module of the apparatus can be configured to determine a diffusion coefficient or a drift coefficient by fitting the solution for $p(\vec{x}, t)$ of a Fokker-Planck equation containing said drift and/or diffusion coefficient with the combined time-resolved signal, and configured to derive the size and/or Stokes radius of the target molecule from the determined drift and/or diffusion coefficient. Note that throughout this disclosure, the "combined time-resolved signal" refers to the average time-resolved signal that is generated from a large number of consecutive switching steps as referred to in steps (A) and (B) above.

It is seen that this rather simple model allows to already capture the essential physics behind the switching step and that it can be used to determine the size and/or Stokes radius of the target molecule from the experimental data with great precision. This will be further demonstrated with reference to a specific example below.

In a preferred embodiment, the analysis module is configured to evaluate the effective Stokes radius, the size and/or the molecular weight of the target molecule. In addition or alternatively to the above, the analysis module may also be configured to evaluate the shape of the target molecule, in particular the folding state and/or a deviation from a globular structure. A deviation from a globular structure can for example be detected by a deviation of the signal from predictions of an analytical model or simulation data based on a globular target molecule.

Further, the analysis module may be configured to evaluate or detect the addition of further molecules to the target molecule.

Since the time resolved switching dynamics will depend on the temperature and the chemical environment of a fluid environment of the probe molecules, the combined signal can also be employed to determine changes in these characteristics of the environment. Conversely, the influence of the environment, such as temperature or pH, on the properties of the target molecules can also be determined, for instance the temperature induced unfolding of a protein.

In a preferred embodiment, the electric field generating means of the apparatus comprises a wave form generator configured to generate a square wave signal switching between a first and a second polarity. Herein, the period of the first and/or second polarity is chosen long enough such that the probe molecules can acquire the respective states of maximum and minimum distance between the second portion and the substrate, respectively. Note that this is just the opposite of the prior art frequency response method, where the target molecule characteristics are revealed by the behaviour at a frequency where the probe molecule can no longer follow the external AC field. Also, in the frequency response method, a sine wave field is used rather than a square wave. It should be noted that while in the setup of FIG. 1, a slow square wave potential is applied to the work electrode 16, in this case only the amplitude in the two polarization states is measured, but there is of course no time resolved measurement of the up and down transition between these states.

Preferably, the period of the first and/or second polarity of the square wave signal is at least 1 µs, preferably at least 10 µs.

Preferably, the control means are adapted to repeat steps (A) and (B) at least 10 times, preferably between $10^3$ to $10^7$ times before the recorded signals are combined. Hence, in a preferred embodiment, it is possible to record time-resolved measurements of a million up and down transitions during only about 1 min, thus allowing to obtain good quality averaged data in a short time, making the apparatus and method especially attractive for routine applications in research or industry laboratories.

In a preferred embodiment, the detecting means of the apparatus comprises a detector for detecting single photons emitted from a fluorescence marker and means for determining the time delay or interval between the switching of said external electric field between steps (A) and (B) and the detected photon. Herein, the control means is further configured to record each time interval in a histogram.

This embodiment is based on the observation that in view of the rather fast switching times, the probability of registering more than one photon or a few photons per up or down transition is not very high, thus allowing for a time-resolved measurement based on single photons. Even if there are more than one photon during one transition, they can be detected individually with a suitable circuitry allowing to measure multiple photon events after a single trigger. The only limitation in this regard is the so-called dead-time of the circuitry, i.e. the period of inactivity of the circuitry after a photon event is detected. Since thousands or even a million of up and down transitions can be measured, the resulting histogram will still record sufficient events to reliably reflect the time-resolved transition dynamics.

In a preferred embodiment, the detecting means may comprise a ramp-generator operatively coupled with the electric field generating means such as to receive the switching of the electric field between steps (A) and (B) as a first trigger signal causing the ramp-generator to start building up a voltage. The ramp-generator is also operatively coupled with the detector such as to receive the detection of a photon as a second trigger stopping the voltage build up, wherein the built up voltage is at least approximately proportional to the time difference between the two triggers.

Note that such a setup is generally known from so-called time-correlated single photon counting (TCSPC) applied in fluorescence measurements, where the first trigger would be the excitation laser pulse and the second trigger would typically be the reception of a fluorescence photon, and where the time delays between excitation and fluorescence would be on the order of a few ns only. However, the inventors confirmed that the TCSPC concept can also be very advantageously applied in the surface-base molecular dynamics measurement of the invention. In particular, while the earlier time-resolved measurements of the inventor for DNA only, i.e. without a capturing probe or a binding of target molecules, would not have suggested that such time-resolved measurements would be feasible for a quick and routine measurement, employing this TCSPC technique in fact allows for a very robust and reliable implementation and short analysis times.

In an alternative embodiment, the detecting means may comprise an amplifier for amplifying the analogue signal indicative of the distance of a second portion of the probe molecule from the substrate. If the signal is the fluorescence signal of a fluorescence marker, then the amplifier could be an amplifier amplifying the signal of a photo sensor. Further, the apparatus may comprise means for recording and storing the time-dependent amplified signal, in particular a digital storage oscilloscope (DSO) type device. The recording and storing means is operationally coupled with the electric field generating means to be triggered to record the time-dependent signal by the switching of the external field between steps (A) and (B), and the recording and storing means is configured to combine the time-dependent signals to generate an average time-resolved signal.

The inventors have confirmed that alternatively to the TCSPC-method, the time-resolved signal can be measured in a series of analogue measurements using a digital storage oscilloscope (DSO) type device. The term "DSO type device" indicates that in principle an ordinary DSO could be used, although of course the display functionality of the DSO is not needed. Instead, all that is needed is the DSO's capability of a triggered recording of a time-dependent signal and the storing thereof.

The individual signals recorded are then added up to give a combined average signal. Again, by superimposing thousands or a million signals, a combined signal of sufficient quality for a meaningful analysis can be obtained. The analogue detection approach also allows for a robust setup and short detection times.

As mentioned before, according to a second aspect, a method for evaluating one or more characteristics of a target molecule bound to a probe molecule is provided. Alternatively or in addition to the above, the apparatus of the invention may comprise means for carrying out a method according to any of the method claims enclosed herewith.

While the apparatus and method described above are specifically devised for a time-resolved measurement of the molecule switching dynamics as such, it is also possible to determine one or more of the following parameters from a plurality of combined signals obtained at different times and/or at different concentrations of target molecules: a binding rate and/or dissociation rate between the target and probe molecules, an affinity constant and a dissociation constant. In these measurements, a parameter indicative of the switching dynamics may be continuously sampled in short time intervals (e.g. 1 second) and monitored over time. Examples for such "switching dynamics" parameter are the integrated area under time-resolved curves (cf. FIGS. 8 & 9), or the real-time calculation of the time-derivative of the "stand-up" process from the time-resolved curves. Changes in these switching dynamics parameters over time are indicative of the binding/unbinding of target molecules of the probe layer in real-time. The data can be analyzed with standard models describing the binding kinetics of bi-molecular system. Association/dissociation rate constants as well as affinity constants can be inferred from such an analysis.

According to a further aspect of the invention, the charge of the target molecule can be determined based on a measurement and an analysis of the dependency of the signal indicative of the distance of the second portion of the probe molecule from the substrate on a static external field. The dependency of the signal on the static external field is referred to herein as the "voltage response". As will be demonstrated below, it turns out that the voltage response is a very sensitive tool to determine the charge of a target molecule bound to a probe molecule. The proposal of the "voltage response" method is influenced by the better understanding of the stochastic nature of the processes described above. In particular, depending on the charge of the target molecule, the voltage response curve will deviate in a characteristic way from the voltage response curve of the free probe molecule alone. Accordingly, by observing the deviation of the voltage response curve when a target molecule is bound from the voltage response curve of the free probe molecule alone, the polarity and even the size of the charge of the target can be determined.

Needless to say, an independent assessment of the target charge by means of the "voltage response method" yields very important additional information that will assist in an educated analysis of the time-resolved data described above. Note that this aspect of the invention does not rely on time-resolved measurements, and it can hence be employed independently of the time-resolved measurement of the switching dynamics as described above. Accordingly, this aspect can also be combined with prior art switch SENSE schemes, including schemes based on an analysis of the frequency response of the switching dynamics, as have been explained with reference to FIG. 2 above.

Consequently, according to a further aspect of the invention, an apparatus is provided which allows to determine the charge of a target molecule, said apparatus comprising: means for receiving a biochip, said biochip comprising a substrate to which probe molecules are attached with a first portion thereof, said probe molecules being charged and having a marker for allowing to generate signals indicative of the distance of a second portion of said probe molecule from said substrate, said probe molecule being adapted to bind said target molecule, means for detecting said signal generated with said marker, means for generating an external electric field which said probe molecules are exposed to when said biochip is received in said receiving means, a control means configured to control the electric field generating means to apply a sequence of static external fields with different field strengths, wherein the control means is further configured to control the signal detecting means to record said signal indicative of said distance from said substrate as the function of external field strength, or—in other words—the voltage response curve, and an analysis module for analyzing the recorded signals and to determine the charge of the target molecule based thereon. Herein, as mentioned before, the analysis may include comparing the measured voltage response curve with the voltage response curve of the free probe molecule, i.e. without a target molecule bound thereto. This further aspect also relates to a corresponding method of determining the charge of a target molecule based on the voltage response curve.

However, the apparatus described above which is adapted for carrying out the time-resolved measurements, generally has all the prerequisites it takes to record the voltage response curves. Accordingly, in a preferred embodiment, voltage response curves are recorded in addition to the time-resolved measurement of the switching dynamics, and the result of the voltage response curves, i.e. information about the charge of the target molecule, can be accounted for in the analysis of the time-resolved combined switching signals.

Based on the above functionalities, the apparatus and method of the invention provide a very powerful analysis means. In particular, the apparatus and method allow to determine one or more of the following:
    the presence of a certain target molecule in a sample,
    the concentration of a target molecule in a sample,
    the fraction of probe molecules occupied by a given target molecule, or
    the stoichiometric ratio of different target molecules that can bind to the same probe molecule capture part, or of the same target molecules in different configurations.

Herein, the term "target molecule" (singular) refers to the species of target molecules. It is understood that always a plurality of target molecules of the same species will be detected.

For example, if only one given target molecule is present in a sample, the combined signal will have a characteristic shape indicative of at least the charge and the Stokes radius of the target. By comparing the combined signal with a predetermined signal for a given target, the presence of a certain target molecule in a sample can be identified.

In some instances, in particular for lower concentrations of target molecules, only a fraction of the probe molecules will be occupied by a given target molecule. In this case, both, the free probe molecules and the occupied probe molecules will add to the combined signal. Since the contributions to the signal add up linearly, the total signal will be a superposition of the signals of the free probe molecules and those of the occupied probe molecules, where the coefficients of the superposition will depend on the fraction of probe molecules occupied by the target molecules. For example, if the fraction of occupied probe molecules was 70%, in the superposition, the coefficient of the signal for the occupied probe molecules would be 0.7 and the coefficient of the signal for the free probe molecules would be 0.3. In practice, when a certain combined signal is measured, the corresponding coefficients of the superposition can be determined by a fitting process such that the superposition coincides best with the measured combined signal. This way, the fraction of occupied probe molecules can be determined. Since the fraction of occupied probe molecules is related to the concentration of the target molecules, it can be used as a measure of the concentration of the respective target molecule.

The same principle and line of reasoning can also be applied for determining the stoichiometric ratio of different target molecules that can bind to the same probe molecule capture part, or of the same target molecules in different configurations. Herein, different configurations could for example be different folding states of a protein that will lead to a different Stokes radius and hence a different switching dynamics, as will be explained in more detail below.

Note that since the different target molecules bind to the same receptor or capture part of the probe molecule, there is no affinity selectivity by which the stoichiometric ratio could be discerned otherwise. However, if the time-resolved signals for the different target molecules, or for the different configurations of the same target molecule, are known, again the coefficients of a superposition of the corresponding signals can be determined that fit the measured combined signal. Herein, the "coefficients of the superposition" directly reflect the stoichiometric ratio.

BRIEF DESCRIPTION OF THE SEVERAL VIEWS OF THE DRAWINGS

FIG. 1 A-D is taken from prior art document 1 illustrating the concept of detecting the presence of target molecules by the switchSENSE method.

FIG. 2 A-B is taken from prior art document 1 and shows the frequency response of the switching dynamics of pristine DNA and DNA with IgG (sheep) bound to it.

FIG. 17A shows time-resolved fluorescence curves obtained for different concentrations of target molecules.

FIG. 17B is a graph illustrating how stoichiometric ratios of different target molecules can be determined by determining a superposition of known time-dependent fluorescence signals for the individual targets.

DESCRIPTION OF THE PREFERRED EMBODIMENTS

Figure 3C:
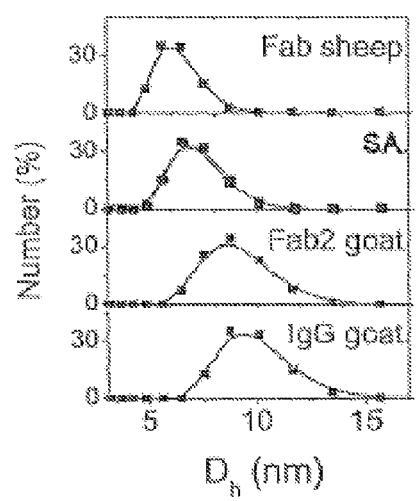
FIG. 3 A-C is taken from prior art document 1 and shows normalized cut-off frequencies for DNA with proteins of varying sizes bound to it.
Figure 3B:
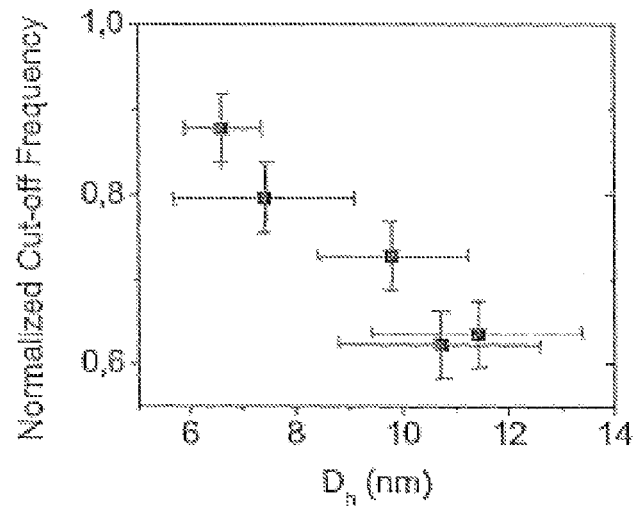
Figure 3A:
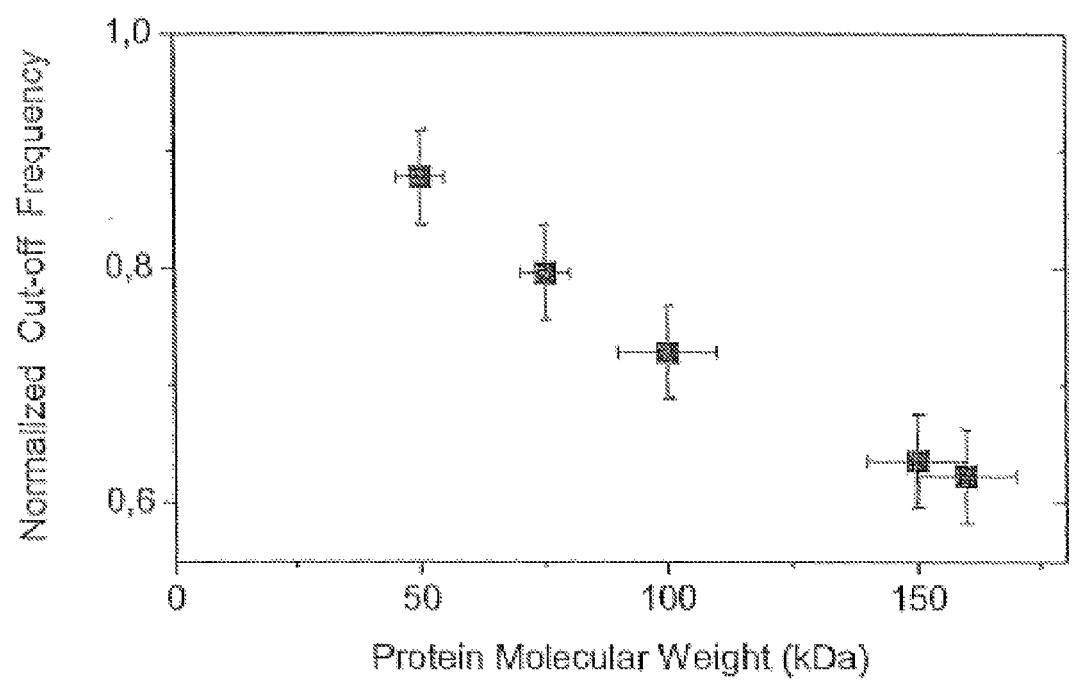

For the purposes of promoting an understanding of the principles of the invention, reference will now be made to the preferred embodiments illustrated in the drawings and specific language will be used to describe the same. It will nevertheless be understood that no limitation of the scope of the invention is thereby intended, such alterations and further modifications in the illustrated apparatus and method, and such further application of the principles of the invention as illustrated therein being contemplated as would normally occur now or in the future to one skilled in the art to which the invention relates.

Figure 4:
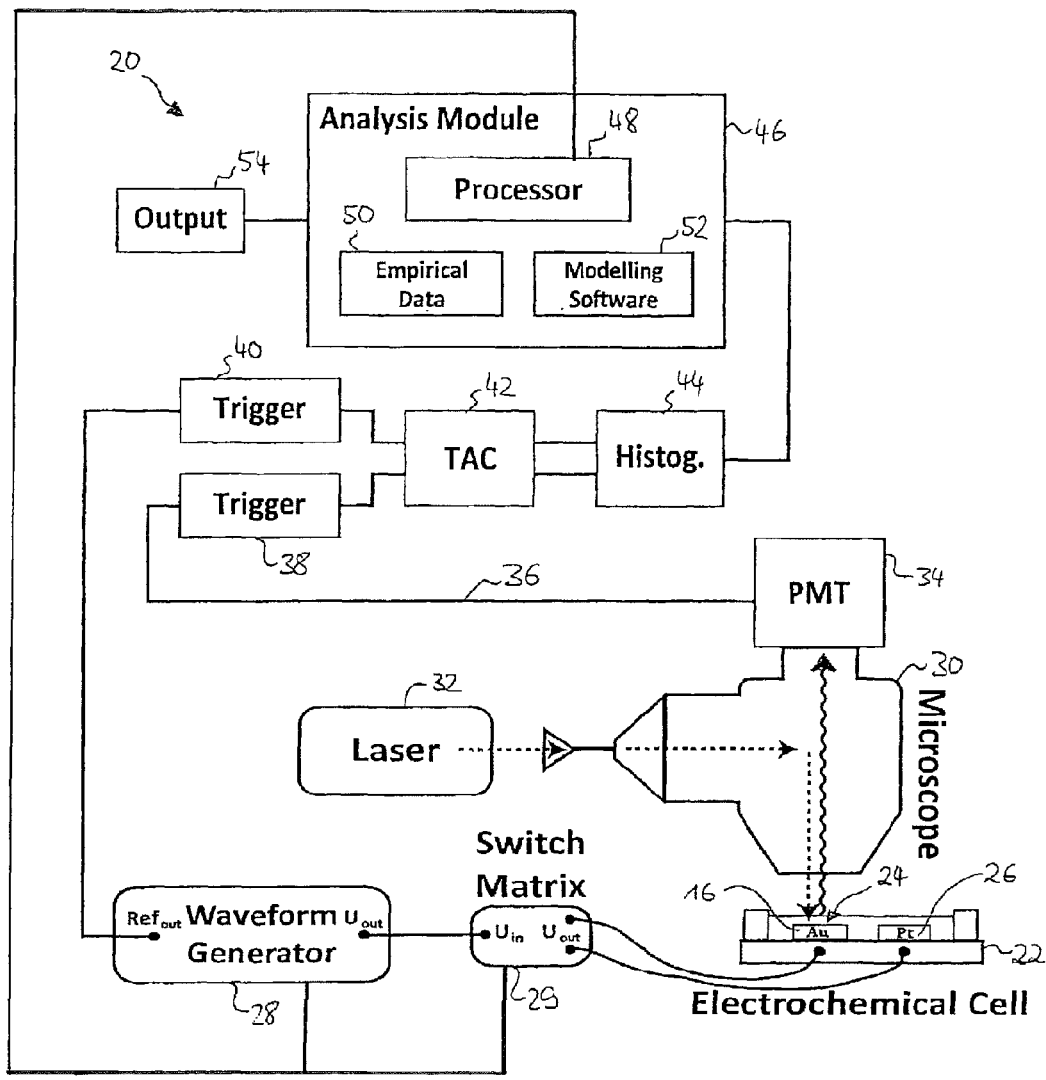
FIG. 4 is a schematic diagram of an apparatus according to an embodiment of the invention based on single photon counting.

In FIG. 4, a first embodiment of an apparatus 20 for evaluating one or more characteristics of a target molecule is schematically shown.

As is shown in FIG. 4, the apparatus 20 comprises an electrochemical cell 22 adapted to receive a biochip 24 which is immersed in a liquid. The liquid could for example be an aqueous solution, such as pH-buffered electrolyte solutions, or complex physiological media, such as blood serum, cell lysate or the like. The biochip 24 comprises a gold work electrode 16 to which probe molecules are attached with a first portion thereof in a way similar to the panel C of FIG. 1. In the shown embodiment, the probe molecules have a fluorescence marker such as fluorescence marker 12 as shown in panel C of FIG. 1 allowing to generate signals indicative of the distance of the fluorescence marker from the gold electrode 16 due to fluorescence quenching, as described in the introductory part of the specification. In addition, a counter electrode 26 made from platinum is provided in the electrochemical cell.

The apparatus 20 further comprises a wave form generator 28 and a switch matrix 29 for applying a time-dependent bias between the work electrode 16 and the counter electrode 26.

As is further shown in FIG. 4, a microscope 30 is provided for receiving fluorescence light from the fluorescence marker. Also, a laser 32 is provided for exciting the fluorescence marker 12.

As is further shown in FIG. 4, a photo multiplier tube (PMT) 34 is coupled with the microscope 30. The PMT 34 is capable of detecting a single photon and to output a signal via signal line 36 in response to the single photon detection. It is to be understood that instead of a PMT, other photon counting detectors can be employed, such as an avalanche photo diode (APD) or the like.

The PMT 34 is coupled with the trigger device 38 via a signal line 36. A further trigger device 40 is provided which is operatively coupled with a wave form generator 28. Both trigger devices 38, 40 are connected with a time-to-amplitude converter (TAC) 42. The TAC 42 is a highly linear ramp generator that is started by a signal from trigger device 40 and stopped by a signal from trigger device 38 and as a result outputs a voltage that is proportional to the time difference between the two signals.

The output of TAC 42 is coupled with a histogramming device 44. The histogramming device 44 is in turn coupled with an analysis module 46 comprising a processor 48 and storage means 50 for empirical data and storage means 52 for modelling software. Finally, the output of the analysis module 46 is connected with an output device 54, such as a display.

Next, the operation of apparatus 20 will be described.

The wave form generator 28 generates a square wave signal with a period of for example 100 µs, switching from positive to negative polarity or vice versa every 50 µs. This square wave potential is applied between the work electrode 16 and the counter electrode 26. In response to this signal, probe molecules such as probe molecules 10 shown in FIG. 1C will switch between the standing and lying configurations back and forth. The trigger device 40 is operatively coupled with the wave form generator 28 and inputs a trigger signal to the TAC 42 each time the square wave signal switches its polarity. The trigger signal from the trigger device 40 causes the TAC 42 to build up a charge at a strictly linear rate.

During the switching of the probe molecules, the laser 32 excites the fluorescence markers such as markers 12 of FIG. 1C. Single photons of the fluorescence light are detected with the PMT 34. If a photon is detected, the trigger device 38 will stop the charge build-up of the TAC 42. Hence, the charge that is built up in the TAC 42 will correspond to a time between the flank of the square wave signal, i.e. initiation of the switching transition, and the photon detection.

If the square wave is applied for e.g. 100 s, one million up transitions and one million down transitions will take place, and during each of these transitions photons will be detected. For each detected photon, a corresponding time value is obtained by the TAC 42, and each time value is recorded in a histogram by the histogramming device 44. In particular, each time the histogramming device 44 receives the time value from the TAC 42, it increases a count for the corresponding time bin. As a result, the histogram represents a time-resolved fluorescence measurement, where the time resolution is only limited by the bin size.

Figure 6:
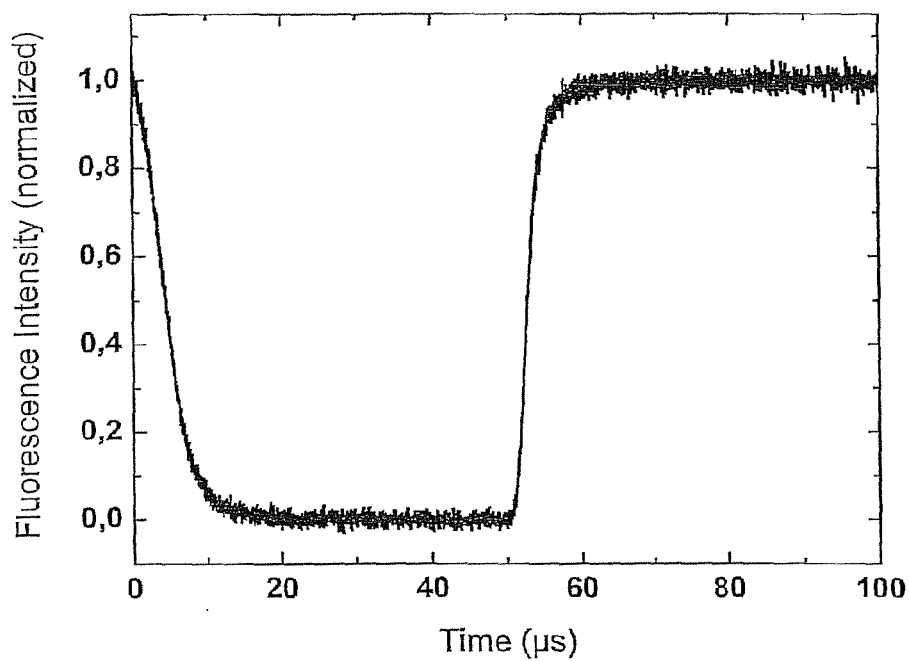
FIG. 6 shows the results of a time-resolved fluorescence measurement of a pristine DNA layer.

An example of such a histogram is shown in FIG. 6, where the normalized fluorescence intensity for a 72 basepair DNA layer modified with a protein receptor but without any target molecules bound thereto is shown.

The time-resolved fluorescence intensity is inputted into the analysis module 46 where it is analyzed and processed such as to evaluate characteristics of target molecules bound to the probe molecules in a way described in more detail below. The result of the analysis is then outputted by the output device 54.

Figure 5:
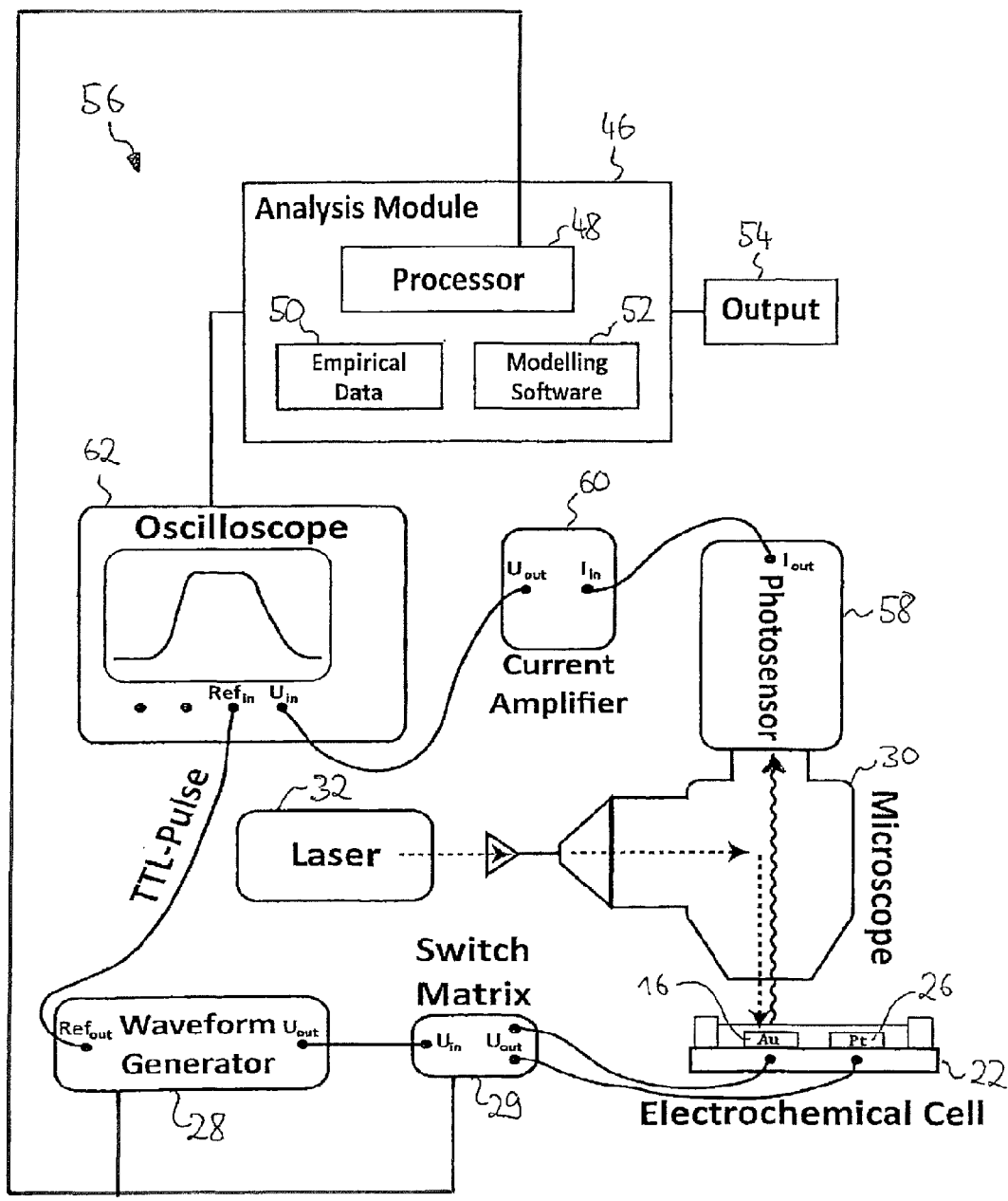
FIG. 5 is a schematic diagram of an apparatus according to an embodiment of the invention based on a measurement of analogue signals.

In FIG. 5, an alternative embodiment 56 of an apparatus according to the invention is shown. Like and similar components of the apparatus 56 are provided with identical reference signs as in the apparatus 20 of FIG. 4, and the description thereof is omitted. In the apparatus 56, instead of a PMT 34, a photo sensor 58 is provided, which generates a photo current in response to receiving fluorescence light. The photo current is amplified by a current amplifier 60 and fed into an oscilloscope 62, which is a digital storage oscilloscope (DSO). The DSO 62 is also operatively coupled with the wave form generator 28. The DSO 62 is triggered by the transition or flank of the square wave signal of the wave form generator 28. Starting from this transition, the oscilloscope records and stores the amplified current signal provided by the photo sensor 58 and the current amplifier 60. In other words, in this embodiment, the input to the DSO 62 is an analogue signal indicative of the fluorescence intensity, which is recorded as a function of time, namely the time from the last transition of the wave form.

Again thousands or a million of switching cycles are carried out, and in each of these cycles, the fluorescence intensity is recorded as a function of time. The signals are added up by the DSO 62 such as to generate a combined signal representing an average time-resolved fluorescence signal similar to the one shown in FIG. 6.

While a DSO 62 is employed in the setup of FIG. 5, it goes without saying that the displaying function of the oscilloscope 62 is not needed, as only the DSO's capability of recording and storing time-dependent signals is employed.

The combined time-resolved fluorescence signal is then inputted into the analysis module 46 which is identical with the analysis module 46 of the embodiment of FIG. 4.

The inventors have built and tested both the apparatus 20 of FIG. 4 and the apparatus 56 of FIG. 5 and found that with such a setup, a time-resolved measurement of the up and down transition process can be measured in short times on the order of 1 min and with a combined signal quality based on thousands or millions of switching transitions that will allow a meaningful analysis of the time-resolved switching dynamics.

Figure 7:
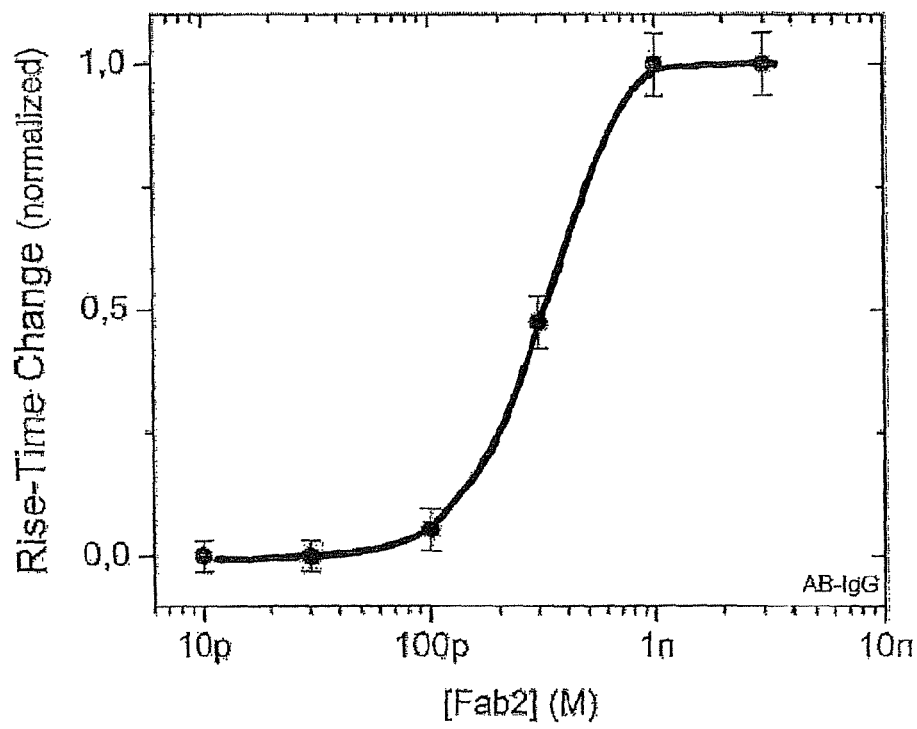
FIG. 7 is a diagram showing the normalized rise-time change as a function of target molecule concentration.

Next, experimental results obtained with the apparatus 20 of FIG. 4 will be discussed. In FIG. 7, a diagram of the rise-time change versus the concentration of a Fab2 fragment of an antibiotin IgG is shown. Upon binding of the Fab2 to the DNA probe molecule, the rise-time of the probe molecule from the lying to the standing configuration increases from 3 µs to 8 µs (see FIG. 8 below). By observing the rise-time change at different concentrations, the dissociation constant $K_D$ can be determined. At high target concentrations, a saturated rise-time value (8 µs) is observed, which stays constant when further increasing the concentration of target molecules. This value is associated with a 100% coverage (saturation) of probe molecules with targets. The initial, i.e. short, rise-time of the bare probe layer is associated with 0% target coverage. Intermediate coverage values for varying target concentrations can be calculated from the rise-time values of the 0% and 100% coverages, respectively, which yields a so-called titration curve as shown in FIG. 7. By fitting the law of mass action (Langmuir isotherm) to the titration curve, the $K_D$ value is obtained.

Figure 8:
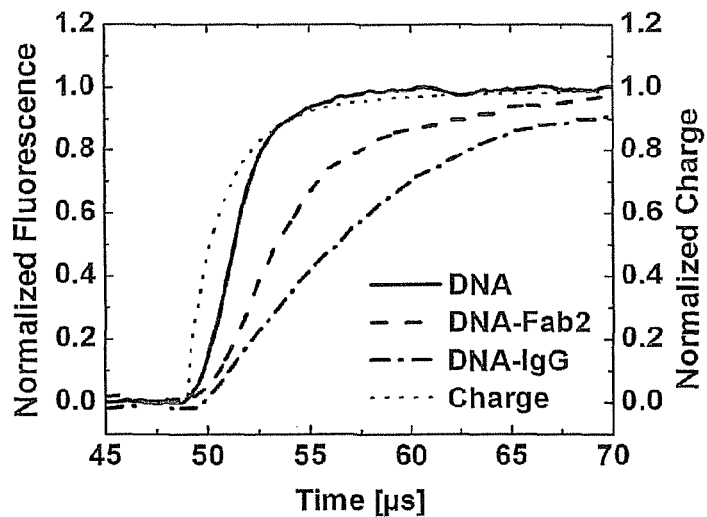
FIG. 8 shows normalized time-resolved fluorescence signals for pristine DNA and DNA where a complete IgG antibody or a Fab2 antibody fragment have been bound to biotin protein receptors.

In FIG. 8, the time-resolved normalized fluorescence for the up transition is shown for the DNA with a protein receptor (biotin) attached to the top (upper curve), for the DNA when a Fab2 antibody fragment of a molecular weight of 100 kDa is bound to the biotin protein receptor (middle curve), and for a case where the complete IgG antibody with a molecular weight of 150 kDa is bound to the biotin protein receptor (lower curve). Also shown in FIG. 8 is the charge of the work electrode as a function of time, showing that the charge does not correspond to a true step function but also suffers from some finite time constant.

As can be seen from FIG. 8, the various target molecules as bound to the probe molecule can be clearly distinguished from each other and be distinguished from a state where no protein is bound at all. According to a preferred embodiment of the invention, the time-resolved measurements are automatically analyzed by the analysis module 46 such as to determine characteristics of the target molecule bound to the probe molecule. For example, the analysis module 46 could determine the time delay between the switching of the polarity of the external field and the time the normalized fluorescence signal reaches a predetermined threshold value, for example 50% thereof, which may be used to represent the rise-time of the probe molecule from the lying to the standing configuration. Such rise-time value is correlated with the size or effective Stokes radius of the target molecule. Accordingly, the analysis module 46 could determine an estimated effective Stokes radius from the rise-time and output it via the output device 54.

Rather than determining the rise-time, for reasons given in the summary of the invention, it may be preferable to determine the derivative of the normalized fluorescence which is indicative of the rising speed of the probe molecule and is expected to be a better indicator of the effective Stokes radius. In particular, in a preferred embodiment the maximum of the time derivative of the normalized fluorescence can be determined, which is indicative of the maximum speed the probe molecule acquires upon the up transition. Since it is believed that the hydrodynamic drag limits the maximum speed, the maximum speed will be a more direct measure of the hydrodynamic drag or effective Stokes radius than the rise-time, which may be influenced by other phenomena as well, including stochastic events.

However, it is also apparent from FIG. 8 that much more information is contained in the time-resolved fluorescence, as it actually reflects the entire time-resolved dynamical behaviour. Accordingly, the analysis module 46 may be configured for more sophisticated types of analysis, taking into account the stochastic nature of the electrically driven probe/target motion as described in the upcoming publication mentioned above.

In one embodiment, empirical data for known targets are stored in a storage 50, and the analysis module 46 can automatically compare the time-resolved fluorescence signal with empirical signals of known targets, thereby allowing to identify target molecules with greater certainty. In cases like this, the analysis module may not only output a characteristic of the target molecule, such as the effective Stokes radius, but can even identify the target molecule itself or output a confidence value that the measured target molecule indeed coincides with the assumed target molecule.

In addition or alternatively, the analysis module 46 may also compare the measured time-dependent fluorescence of the up or down transition with data obtained from a model calculation, as has been explained in the summary of the invention. Again, a comparison with a model calculation may help to identify a target molecule or at least to give a confidence value that a certain target molecule identification or a characteristic of the target molecule as presented by the analysis module 46 is correct.

Figure 11:
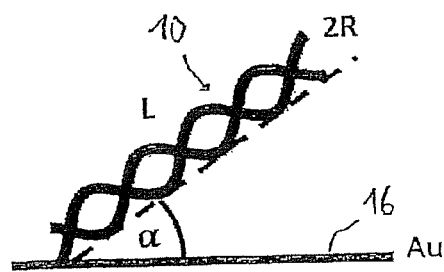
FIG. 11 shows a schematic representation of a model for modelling a double-stranded DNA probe molecule.

According to one embodiment, the probe molecule is a double-stranded DNA which is modelled as a charged rigid cylinder in which the charge is continuously distributed along the cylinder axis, as is schematically shown in FIG. 11. Accordingly, the configuration of the probe molecule 10 can be parameterized by an angle $\alpha$ with regard to the substrate 16 only. Note that the azimuth angle can be disregarded because it does not play any role in the processes observed herein. According to the model, and with further reference to FIG. 11, the length of the DNA is measured in multiples n of lengths b of a single base, where b=0.34 nm. The diameter of the cylinder is 2R with R=1 nm.

The charge q of the DNA depends on the number of bases, i.e. q=−2ne, where e is the elementary charge.

Since a potential is applied to the substrate 16, the DNA experiences an electric field $\Phi(r, \alpha)$, which decays exponentially:

$$\varphi(r,\alpha) = \varphi_{eff} \cdot e^{-\kappa T \sin \alpha}$$

Herein, $\Phi_{eff}$ is an effective potential that corresponds to the applied potential $\Phi$ multiplied with a screening factor $\gamma<1$, i.e. $\varphi_{eff} = \gamma \cdot \varphi$.

The inventors have found out that the dynamics of the probe molecule is to a large extent of stochastic nature. Accordingly, the motion of the probe molecule can be described quite accurately based on Brownian motion with an additional drift due to the applied electric field. To further understand the dynamical behaviour of the probe molecule, the energy $U(\alpha, \Phi)$, the entropy $S(\alpha)$ and the Gibbs free energy $G[\alpha, \Phi]$ for any given conformation, i.e. any given angle $\alpha$ is calculated as follows $$U(\alpha, \phi) = \gamma \cdot \phi \cdot \frac{q}{L} \int_0^L e^{-x(r \sin\alpha + R \cos\alpha)} dr = -\gamma \cdot \phi \cdot \frac{2e}{\kappa b} \cdot \frac{1 - e^{-\lambda L \sin\alpha}}{e^{xR\cos\alpha} \cdot \sin\alpha} + U_0$$

$$S(\alpha) = k_b \cdot \ln\Omega(\alpha) = k_b \cdot \ln(N \cdot 2\pi \cdot L \cdot \cos\alpha) = k_b \cdot \ln(\cos\alpha) + S_0$$

$$G[\alpha, \phi] =$$
$$U(\alpha, \phi) - T \cdot S(\alpha) = -\gamma \cdot \phi \cdot \frac{2e}{\kappa b} \cdot \frac{1 - e^{-xL\sin\alpha}}{e^{xR\cos\alpha} \cdot \sin\alpha} - k_b T \cdot \ln(\cos\alpha) + G_0$$

From this, the following Boltzmann probability distribution can be derived:

$$p[\alpha, \phi] = \frac{1}{Z} \cdot \exp\left(-\frac{G[\alpha, \phi]}{k_b T}\right),$$

with a normalization condition $$\int_0^{\frac{\pi}{2}} p[\alpha, \phi] d\alpha = 1.$$

From the probability distribution, the fluorescence signal can then be calculated as follows:

$$F[\phi] = \int_0^{\frac{\pi}{2}} f[\alpha] \cdot p[\alpha, \phi] d\alpha$$

and $$f[\alpha] = 0.21 \cdot \left(1 - \left(\frac{L \cdot \sin\alpha + 1}{24}\right)^{-2.8}\right).$$

Herein, f[$\alpha$] is an analytical approximation of the height dependent dye fluorescence as described in the *Journal of the American Chemical Society*, 132, 7935 (2010).

Note that so far no time dependence has been introduced, since the electric field has been kept stationary. However, with the above equation, it is possible to calculate the fluorescence signal for different values of the applied static potential $\Phi$. The corresponding curve is referred to as "voltage response curve" in the following.

Figure 12:
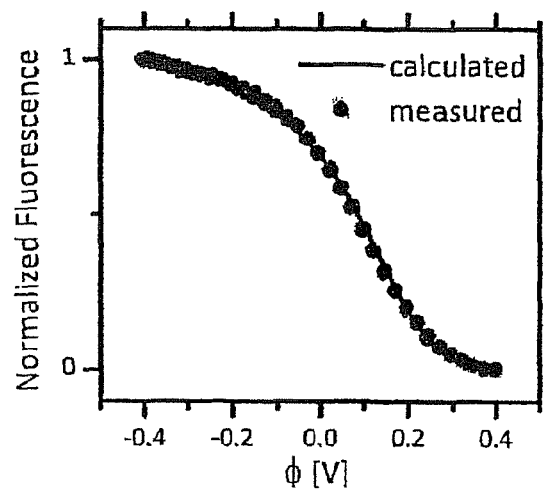
FIG. 12 shows a comparison of the voltage response curves of the free DNA as calculated by the analytical model and as measured in experiment.

FIG. 12 shows a comparison of the voltage response curves as calculated according to the above model and as obtained by experiment. In the calculation, a screening factor of γ=0.018 has been assumed. The agreement between the calculated voltage response according to the above model and the measured data is excellent, which is a strong indication that the above model captures the essential physics correctly. Note that the screening factor γ can be determined by fitting the calculated voltage response curves to the measured curve.

Further note that the model so far only accounted for the free probe molecule, i.e. the double-stranded DNA, but not for any target molecule. As long as the stationary state is concerned, i.e. without a time-dependent electrical field, the target molecule will mainly affect the results due to a possible charge thereof. In fact, based on the above understanding of the stochastic behaviour of the probe molecule, the inventors conjectured that it should be possible to qualitatively and quantitatively determine the charge of the target molecule from the voltage response curve. This has actually been confirmed in experiment, as shown in FIGS. 13 and 14.

Figures 13, 14:
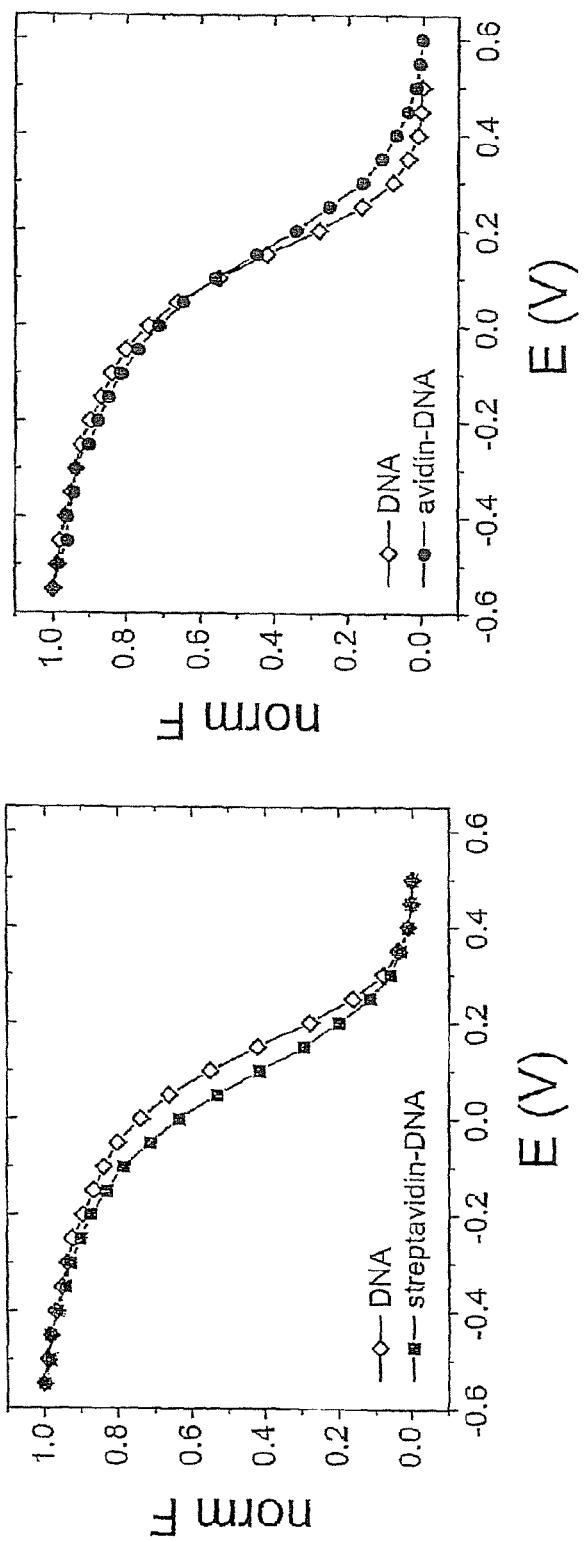
FIG. 13 shows a comparison of the measured voltage response curves of a free DNA probe molecule and the DNA with a streptavidin target bound thereto.
FIG. 14 shows a comparison of the measured voltage response curves of a free DNA probe molecule and the DNA with an avidin target bound thereto.

FIG. 13 shows the normalized fluorescence signal as a function of the static potential applied to the substrate 16, for both, the DNA alone (open diamonds) and the same DNA to which a negatively charged protein, namely streptavidin, was bound (filled squares). As can be seen from FIG. 13, the negatively charged streptavidin obviously has a noticeable effect on the voltage response curve in that the fluorescence signal drops faster with increased substrate potential than in case of the DNA alone. This behaviour is intuitively understandable, since the negative charge of the target molecule will add to the effect of the negatively charged DNA, i.e. cause the probe molecule 10 to approach the substrate 16 when a positive potential is applied thereto.

The opposite case is shown in FIG. 14, where a positively charged protein (avidin) is bound to the probe DNA. The corresponding voltage response curve is shown by filled circles, while the voltage response curve of the free DNA is again shown by open diamonds. It can be seen that the voltage response curve in presence of the avidin also differs noticeably from that of the DNA alone. The qualitative behaviour is again intuitively understandable, as in this case the positively charged target molecule is repelled from the positively charged substrate 16, which causes the voltage response curve to lie above that of the free DNA for positive potentials.

Accordingly, it is seen that the voltage response curve is a very sensitive tool to determine the charge of a target molecule. Since voltage response curves can be recorded easily and quickly, this is the preferred way of determining the charge of target molecules that can be carried out routinely in target molecule analysis.

Note that the charge Q of the target molecule can be easily introduced in the above model by introducing the following additional electrical interaction term into the Gibbs-energy function:

$$\Delta U[\alpha] = Q \cdot \varphi_{\textit{eff}} \cdot e^{-\kappa \cdot L} \sin \alpha$$

So far, the model has only accounted for stationary electrical fields. Once the electrical field Φ is time-dependent, the probability distribution will be time-dependent too, i.e.

$$\varphi(t) = +\varphi_0 + \Delta\varphi \cdot (1 - e^{+t/\tau}), \text{ hence } p[\alpha, \varphi(t)] = p[\alpha, t]$$

Assuming again that the dynamical behaviour of the probe molecule is stochastic in nature, the time dependency of the probability distribution p(α, t) can be described by a Fokker-Planck equation:

$$\frac{\partial p[\alpha, t]}{\partial t} = D_r \frac{\partial^2 p[\alpha, t]}{\partial \alpha^2} + \frac{D_r}{k_b T} \frac{\partial}{\partial \alpha}\left(\frac{\partial G[\alpha, t]}{\partial \alpha} \cdot p[\alpha, t]\right)$$

Herein, the term $$D_r \frac{d^2 p[\alpha, t]}{\partial \alpha^2}$$

is a diffusion term characterizing Brownian motion like behaviour that is governed by a rotational diffusion coefficient $D_r$. The second term is a drift term due to the angle and time-dependent free energy. The above Fokker-Planck equation can be solved numerically for any given time dependence of the electrical field Φ(t).

In order to simulate the DNA switching, one calculates the starting probability distribution and then calculates the time evolution of the probability distribution via the Fokker-Planck equation given above. The solution depends only on the rotational diffusion coefficient $D_r$. Accordingly, $D_r$ can be determined by fitting the model calculations to the experimental data. This way, estimated rotational diffusion coefficients of the free DNA and the DNA with the target molecule bound to its end can be determined. From this, one can in turn calculate the hydrodynamic radius of the attached target molecule using Stokes' law.

Figure 15:
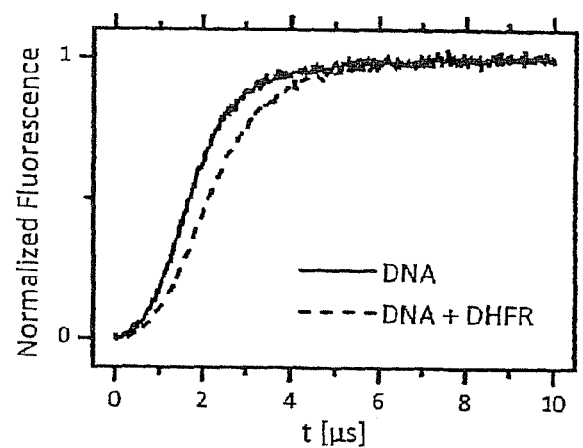
FIG. 15 shows a measurement of the time-resolved fluorescence of a free DNA probe molecule and the DNA with a DHFR target attached thereto.

Again, it is seen that based on this model, the Stokes radius can be determined from the time-resolved signal with great precision. FIG. 15 shows the time-resolved rising curves for bare double-stranded DNA and for the same DNA with the enzyme dihydrofolate reductase (DHFR) bound to its end. As is clearly seen from FIG. 15, the rise time of the DNA with the additional DHFR is retarded due to the friction caused thereby.

Figure 16:
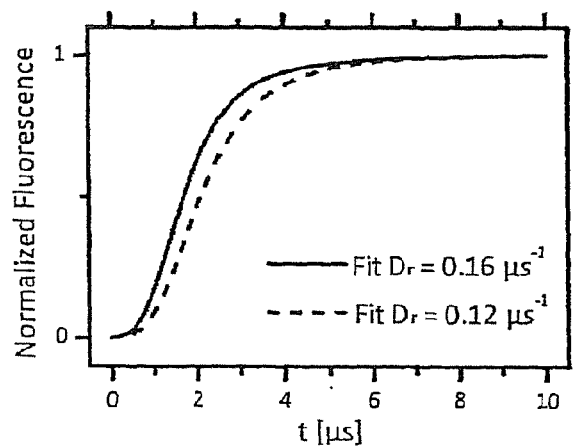
FIG. 16 shows the time-resolved fluorescence for the DNA and DNA plus DHFR of FIG. 15 as calculated based on the analytical model, where the rotation diffusion coefficient has been obtained by fitting to the experimental data.

FIG. 16 shows the two best fits of solutions of the above Fokker-Planck equation, which were found for rotational diffusion radii of 0.12 $\mu s^{-1}$ and 0.16$^{-1}$ $\mu s^{-1}$, respectively. From this, Stokes law yields a hydrodynamic radius of 1.6 nm for the DHFR, which almost exactly matches the literature value of 1.5 nm.

Accordingly, it is seen that the analytical model does not only help to understand the behaviour of the switching, but it can actually be used to determine the Stokes radius of an unknown target molecule from the time-resolved data with rather high precision.

Instead of analyzing the measured data with reference to an analytic model or a simulation, as mentioned before, experimental data can also be compared to stored data sets of known targets. Accordingly, by comparison with known time-resolved data sets, unknown targets can be characterized or even recognized.

Figure 9:
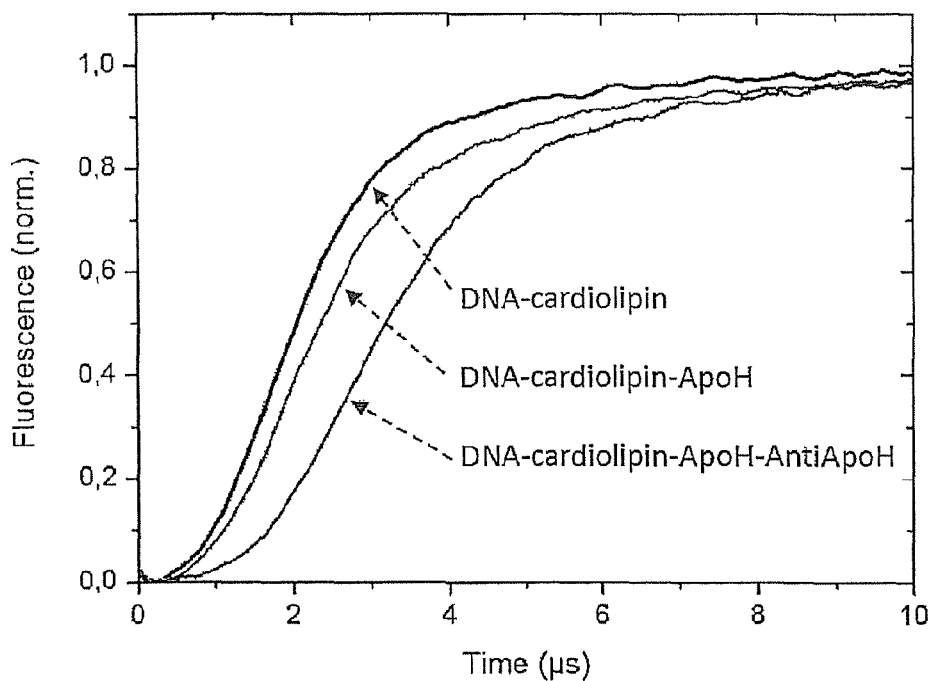
FIG. 9 shows the time-resolved normalized fluorescence signal of a DNA modified with a protein receptor of the DNA after binding of a 50 kDa protein and after binding an IgG antibody to the protein.

FIG. 9 shows yet further examples of time-resolved normalized fluorescence as obtained with the apparatus 20 of FIG. 4. In FIG. 9, the upper graph again shows the fluorescence of the time-resolved upward switching of a DNA modified with a protein receptor, but without any target molecule bound to it. The middle curve shows the time-resolved fluorescence after binding of a 50 kDa protein to it. The lowest curve shows the time-resolved fluorescence after an IgG antibody (150 kDa) is bound to the 50 kDa protein. Again, FIG. 9 clearly shows that binding of multiple targets can be clearly distinguished with the time-resolved fluorescence measurement of the invention.

Figure 10A:
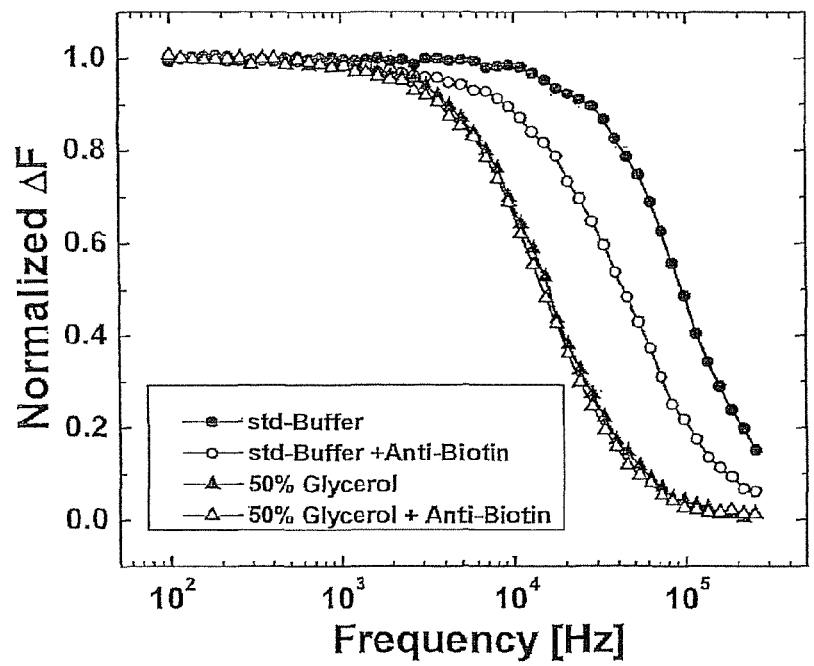
FIG. 10 A-C shows a comparison of results obtained from frequency response measurements according to prior art and time-resolved measurements according to the invention.

Finally, with reference to FIG. 10, a comparison of the results obtainable with the prior art frequency response method and the time-resolved measurement of the invention is shown. In FIG. 10a, the frequency response curve of the pristine probe molecule in standard buffer solution (black circles) and with an IgG antibody bound to it (white circles) is shown. The two curves can be clearly distinguished, and in particular, the effective stokes radius of the IgG antibody can be evaluated by the shift of the cut-off frequency.

However, if the viscosity of the solution is increased by adding 50% glycerol to the fluid environment, the frequency response of the probe molecule with and without the IgG anti-biotin are identical. Accordingly, in this scenario, the anti-biotin binding to the probe molecule can no longer be distinguished.

Figure 10B:
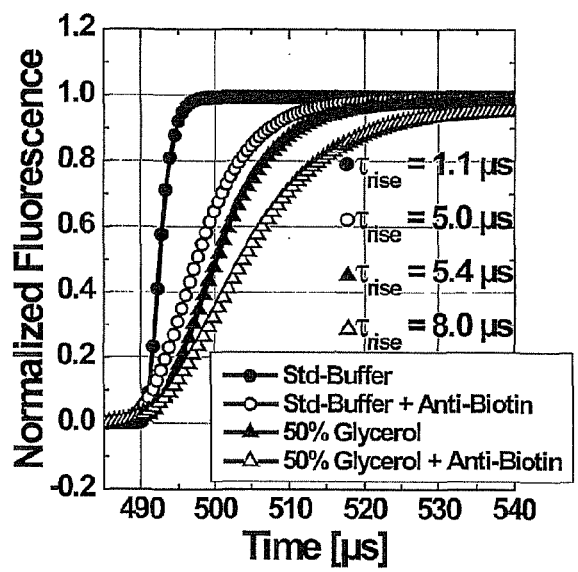
Figure 10C:
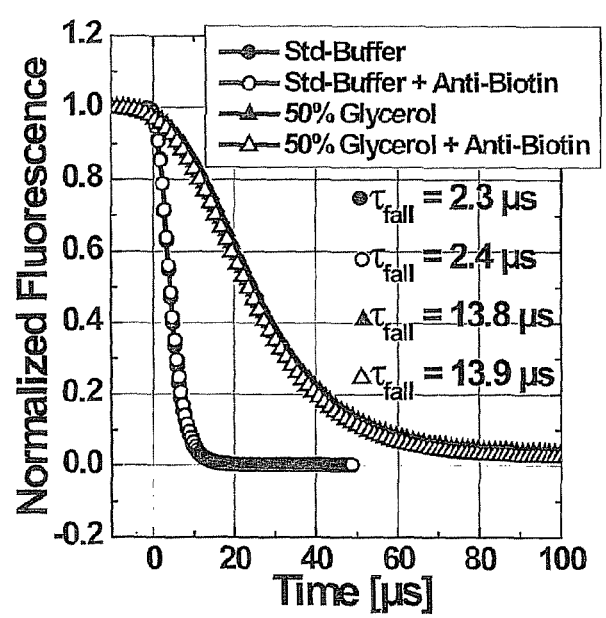

FIGS. 10b and 10c show the time-resolved fluorescence measurements for the same probe and targets for the up transition (FIG. 10b) and the down transition (FIG. 10c).

As can be seen from FIG. 10b, even with 50% glycerol added to the solution, in the up transition the probe molecule with and without anti-biotin can clearly be distinguished, yielding different rise-times of 8.0 µs and 5.5 µs, respectively. However, it is seen that for both buffers, the time-resolved curves with and without anti-biotin in the down transition can practically not be distinguished.

From the time-resolved measurements of FIG. 10b and FIG. 10c it is seen that apparently, the hydrodynamic drag of the anti-biotin governs the dynamics of the up transition, but not of the down transition. This is a result that could not be discerned from the frequency response analysis according to prior art.

What is more, the cut-off frequency will always be governed by both, the time constants of the up and down transitions. In fact, the longer of the two time constants will dominate the cut-off frequency. The effect of this can be seen in FIG. 10a: Although the time constants for the down transitions are nearly identical with or without anti-biotin bound to the probe molecule, the difference in the time constants of the up transition ($\tau_{rise}$) is sufficient to give rise to a shift in cut-off frequency that allows to distinguish the two cases and to even characterize the anti-biotin with regard to its effective Stokes radius. However, when the viscosity of the buffer is increased by adding glycerol, although the rise-times with and without anti-biotin are still different, the cut-off frequency is dominated by considerably increased time constant $\tau_{fall}$ of the down transition to an extent that the frequency response spectra can no longer be distinguished.

So in summary, FIG. 10 demonstrates a surprising and unforeseeable improvement provided by the time resolved measurement of the invention as compared to the frequency response analysis. While instrumental expenditure of the apparatuses 20 and 56 of FIGS. 4 and 5 is hardly increased as compared to an apparatus for carrying out the frequency response analysis, it is a further and surprising result that the time-resolved measurement can be put to practice in a very robust and reliable way and without significantly increasing the time for the analysis. Given the more reliable results and the possibility for a sophisticated analysis by analysis module 46, the time-resolved measurement scheme of the invention is in fact particularly preferable for apparatuses for routine use in laboratories, where detailed and reliable analysis results are to be provided without requiring the user to understand the underlying principle or interpret the measurement results him- or herself.

The method and apparatus of the invention also allows to determine the concentration of certain target molecules in a sample or the stoichiometric ratio of two or more target molecules in a sample. This will be explained with reference to FIGS. 17 and 18.

FIG. 17(a) shows the time-resolved fluorescence signal for different concentrations of target molecules in a sample. The highest curve in FIG. 17(a) corresponds to a concentration of 0 pM, i.e. there are no target molecules in the sample. Accordingly, this curve corresponds to the switching behaviour of the probe molecule 10 alone.

The lowest of the curves are actually two curves that nearly coincide and correspond to target concentrations of 3 nM and 10 nM, respectively. As these two curves coincide, it can be assumed that the biosensor is saturated, i.e. that a target molecule is bound to each of the probe molecules 10. The two curves in-between correspond to intermediate concentrations of 60 pM and 300 pM, and in this case obviously part of the probe molecules 10 are occupied by a target molecule while others are not. Since the fluorescence signal is a linear combination of individual signals corresponding to probe molecules 10 with and probe molecules 10 without target molecules bound thereto, it is expected that the intermediate measured curves correspond to a superposition of the target-free curves and completely target binding curves. The respective coefficients of the superposition would then correspond to the percentage of probe molecules with and without targets bound thereto. For example, if 80% of the probe molecules 10 are occupied by a target molecule, the resulting fluorescence signal curve is expected to be a superposition of the lowermost (i.e. 100% binding) and uppermost (i.e. 0% binding) curves in FIG. 17(a), where the coefficient of the lowermost curve in the superposition would be 0.8 and where the coefficient of the uppermost curve the would be 0.2.

This conjecture is actually confirmed by experiments of the inventors. The inventors have prepared biochips with a plurality of probe molecules 10, on which the receptor density, i.e. the density of capture portions was varied, as is schematically shown in FIG. 17(b). For example, if the receptor density was 50%, only half of the biomolecules 10 actually had a receptor for capturing a target molecule. Using a sample with a high concentration of target molecules, it could then be ensured that all available receptors were actually occupied by a corresponding target molecule. Accordingly, by predetermining the receptor density, effectively the fraction of probe molecules with attached target molecules could be controlled.

In FIG. 17(b), the horizontal axis corresponds to the receptor density, i.e. the percentage of probe molecules 10 having a receptor. For each of these receptor densities, a time-dependent fluorescence signal as shown in FIG. 17(a) was recorded. Then the superposition of the known or expected signal for free probe molecules and for 100%-targeted-probe molecules was determined that fitted the measured curve best. The vertical axis of the diagram of FIG. 17(b) corresponds to the coefficient of the free probe molecule curve in the respective superposition. Accordingly, if the above hypothesis is correct, then all data points should lie on the dashed line connecting the points (0,0) and (1,1) in the diagram of FIG. 17(b). As is seen from FIG. 17(b), this is indeed the case, giving strong support that the hypothesis is correct.

So in summary, by knowing the 0% (i.e. free probe molecule) and the 100% coverage (i.e. completely targeted probe molecule) curves, the target coverage of any curve obtained from experiment can be determined with good precision by determining the corresponding superposition coefficients of the 0%- and 100%-target-coverage-curves.

Further, if it is known how the coverage relates to the concentration of target molecules in the probe solution, then this is a direct measure of the concentration.

The same principle can of course not only be applied to determine the coverage of receptors, but also to distinguish the ratio of different target molecules that bind to the same receptor, in a sample solution.

Figure 18A:
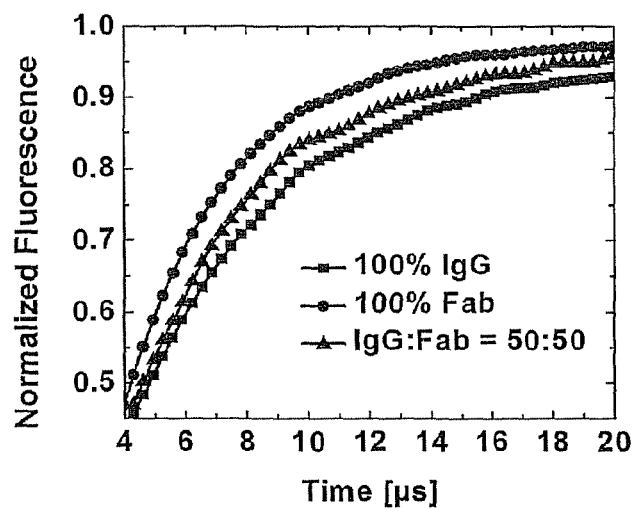
FIG. 18A shows time-resolved fluorescence signals for DNA probe molecules with 100% IgG occupation, 100% Fab occupation and 50% IgG-50% Fab-occupation.
Figure 18B:
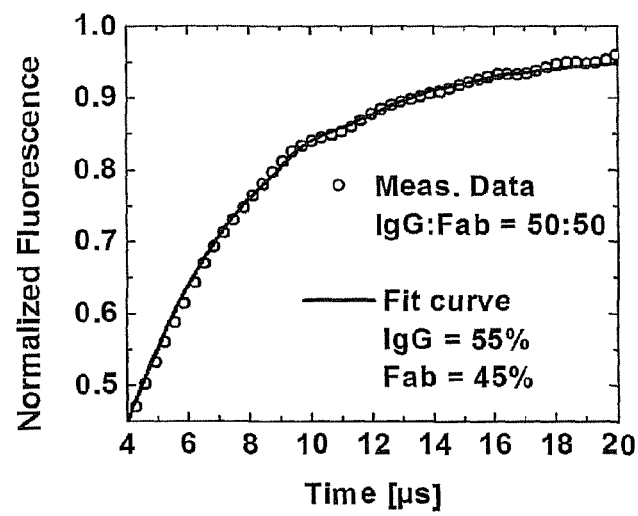
FIG. 18B shows the best fit of the superposition of the individual IgG and Fab time-dependent fluorescence signals to the measured time-dependent fluorescence signal.

For example, the stoichometric ratio of different target molecules that can bind to the same probe molecule receptor can be determined. According to prior art methods, this is hardly possible, since there is no affinity selection if both target molecules bind to the same receptor. According to the invention, however, if the two different target molecules lead to different time-resolved fluorescence curves, that are per se known, then in case of a measured curve (in the same way as described above) a suitable superposition of the target-specific curves can be determined that fits with the experimental time resolved signal, and the corresponding coefficients reflect the stoichometric ratio. An example of this is shown in FIG. 18(*a*). In FIG. 18(*a*), the lower-most curve represents the time-dependent fluorescence of the IgG anti-biotin. The IgG can be fragmented, such that Fab-fragments are separated from the IgG. The Fab-fragments can of course bind to the same receptor (anti-gene) as the whole IgG. However, since the Stokes radius of the Fab-fragment is smaller than that of the IgG, the time-resolved fluorescence curve will rise quicker in the electrical field. Accordingly, the stoichometric ratio of IgG and Fab-fragments can be determined by the coefficients of a superposition of the known IgG-curve and the known Fab-curve that fits best with the experimental data.

This method has been confirmed in an experiment as well. However, in order to be in a position to precisely pre-determine the stoichiometric ratio of IgG and Fab, different receptors (anti-genes) have been attached to the probe molecules 10. Half of the receptors were biotin which are receptors for the IgG anti-biotin, while the other half of the receptors were digoxygenin, which were receptors of anti-digoxygenin Fabs. The upper-most curve in FIG. 18(*a*) hence corresponds to the signal obtained for a 100% coverage of the anti-digoxygenin Fab.

Using a biochip with 50% biotin and 50% digoxygenin receptors, the middle curve in FIG. 18(*a*) was measured. In practice, one would measure a curve like the middle curve in FIG. 18(*a*) and would then want to know the stoichiometric ratio of Fab and IgG. According to the teaching above, one would look for the superposition of the known Fab- and IgG-curves that fit the measured data best. The result of this is shown in FIG. 18(*b*). The thick curve in FIG. 18(*b*) represents the actual fluorescence measurement, i.e. the middle curve in FIG. 18(*a*). The thin line in FIG. 18(*b*) is the best fit for the superposition of the upper and lower curves in FIG. 18(*a*) to the middle curve, which in the present case yielded 55% IgG and 45% Fab, i.e. superposition coefficients of 0.55 and 0.45, respectively which is quite close to 50% IgG and 50% Fab. Accordingly, it is seen that the stoichiometric ratio can be determined with rather accurate position. This is a remarkable result, since in an actual application, there would be no affinity selection, i.e. the different molecules would bind to the same receptors, and there is hence no other practical way of determining the stoichiometric ratio.

This embodiment of the invention will have many practical applications. For example, if an antibody like the IgG above shall be fragmented by adding an enzyme, the percentage of the fragmentization can be determined. Also, if a given molecule can form monomers or dimers, and the time-dependent fluorescence curves for the monomer and the dimer, respectively, are known, then the stoichiometric ratio of the monomers and dimers in a sample can be readily determined.

Figure 19:
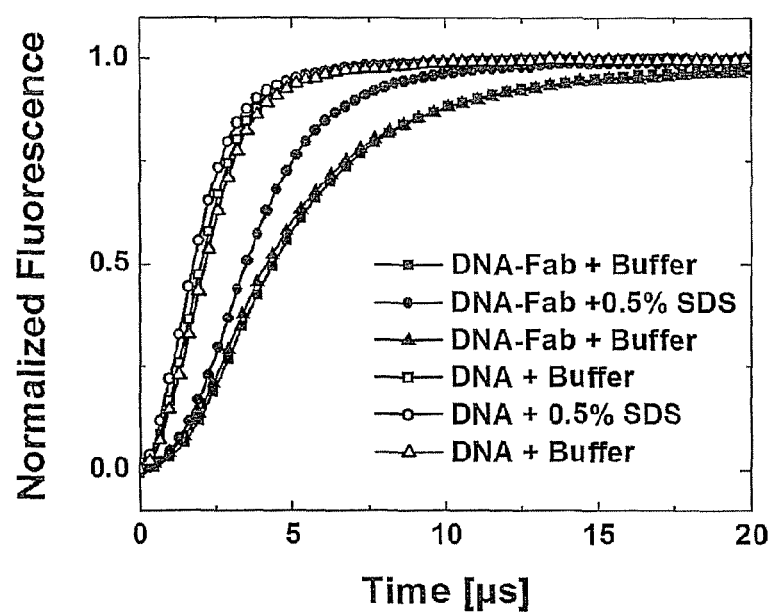
FIG. 19 shows time-resolved normalized fluorescence signals of a DNA probe molecule occupied by folded and unfolded Fab, respectively.

In fact, with this embodiment of the invention, not only the stoichiometric ratio of different target molecules (like Fab/IgG or monomer/dimer), but also the stoichiometric ratio of different configurations of the same molecule can be determined, if the different configurations lead to different time dependent fluorescent curves. An example for this is shown in FIG. 19. FIG. 19 again shows measurements of the time-resolved normalized fluorescence. The upper-most curve corresponds to the probe molecule 10 alone, which in this case again is double-stranded DNA. The lowermost curve corresponds to the probe molecule (DNA) to which a Fab fragment is bound. In the ordinary state, the Fab fragment acquires a "folded state" giving rise to a certain Stokes radius that is responsible for the slower rise of the fluorescence signal as compared to the free DNA.

The middle curve in FIG. 19 corresponds to the same sample, to which, however, a detergent (SDS) is added. The SDS causes the Fab fragment to unfold, as is schematically shown in FIG. 19. In the unfolded configuration, the effective Stokes radius is decreased, thereby leading to a rise time that is between that of the DNA occupied by the folded Fab and that of the DNA alone. Accordingly, the change of the conformation, i.e. folded versus unfolded, can be directly observed by the time-dependent fluorescence signal. After the SDS has been washed out of the solution, it was seen that the Fab fragments acquire their folded configuration again, i.e. the fluorescence signal of the lowest curve in FIG. 19 was observed again. Also, the stoichiometric ratio of folded and unfolded Fabs can be determined by determining the coefficients in the superposition in the same manner as described above.

Figure 20:
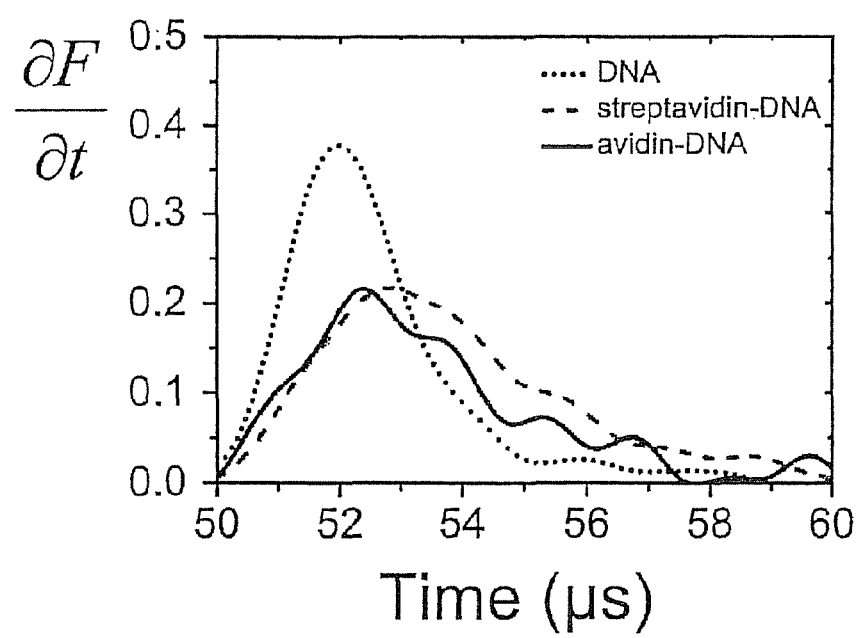
FIG. 20 shows the time-derivative of the normalized fluorescence signal of DNA alone, DNA with streptavidin bound thereto and DNA with avidin bound thereto.

As has been explained above, in many cases the time derivative of the fluorescence signal is a good observable for characterizing the target molecule. In FIG. 20, the time derivative of the fluorescence signal as a function of time is shown for the probe molecule (DNA) alone (dotted line), the probe molecule with a streptavidin target (dashed line) and the probe molecule with a avidin target bound thereto (solid line). Avidin and streptavidin have practically identical size and Stokes radii, but still the time derivative of the fluorescence signal differs noticeably. This difference is due to the charge of the target molecule. The streptavidin, which is negatively charged, will lead to a velocity that remains higher than that of the (positively charged) avidin at least in the second half of the stand-up process. This is intuitively understandable, since the negative streptavidin will support the negative DNA in the stand-up motion, while the positively charged avidin will counteract this motion. Again, this demonstrates that the method according to the present invention is sensitive enough to even distinguish the charge of target molecules from the time-resolved fluorescence signal.

Finally, it is seen that the binding kinetics of the target molecules to the receptor can be measured with very good precision. In FIG. 7, the rise-time change with the concentration of a Fab2 fragment of an antibiotine IgG. was shown. From this, the dissociation rate $K_D$ or its inverse, the affinity rate $K_A$ can be determined. As is well-known, the dissociation rate $K_D$ corresponds to the ratio of backward rate ($k_{off}$) and forward rate ($k_{on}$), i.e. $K_A = \frac{1}{K_D} = \frac{k_{on}}{k_{off}}$.

However, in the framework of the present invention, it is also possible to measure $k_{on}$ and $k_{off}$ directly. For this, in FIG. 21, the maximum value of the derivative of the normalized fluorescent signal, referred to as "$V_{max}$", is shown after the probe molecules have been exposed to the target (panels A, C and E) or after the exposure to the target molecules was terminated (panels B, D and F).

$V_{max}$ is found to be a very sensitive indicator for analyzing whether a target molecule is bound to a probe molecule or not. As the probe molecules are exposed to the target molecules, the target molecules will bind to the probe molecules with the forward rate $k_{on}$, thereby slowing down the switching dynamics and reducing $V_{max}$. As is seen in panels A, C and E, $V_{max}$ decays exponentially as the probe molecules are occupied by the target molecules with a rate that resembles $k_{on}$.

Figure 21:
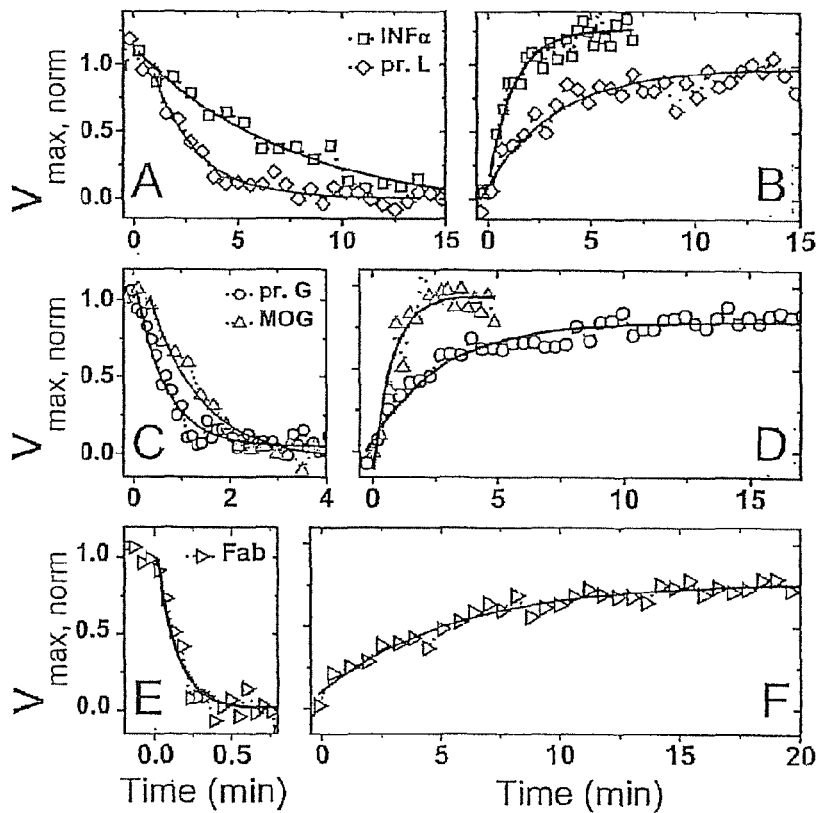
FIG. 21 A-F shows measurements revealing the forward and backward rates of the binding kinetics for different proteins.

Conversely, after the exposure to target molecules is terminated, $V_{max}$ again increases according to $1-e^{-k_{off}t}$ FIG. 21 shows the binding kinetics for proteins A, G, L, INFα, MOG and Fab, where the corresponding forward and backward rates $k_{on}$, $k_{off}$ are summarized in a table. Again, it is seen that the apparatus and method according to the present invention not only allow determining the dissociation or affinity rates $K_D$, $K_A$, respectively, but also the underlying forward and backward rates $k_{on}$, $k_{off}$ with great precision.

Although preferred exemplary embodiments are shown and specified in detail in the drawings and the preceding specification, these should be viewed as purely exemplary and not as limiting the invention. It is noted in this regard that only the preferred exemplary embodiments are shown and specified, and all variations and modifications should be protected that presently or in the future lie within the scope of the appendant claims.

REFERENCE SIGNS 10 probe molecule
12 marker
14 protein binding tag
16 work electrode
18 biasing means
20 apparatus for evaluating characteristics of target molecules
22 receiving means
24 biochip
26 counter electrode
28 wave form generator
29 switch matrix
30 microscope
32 laser
34 photo multiplier tube
36 signal line
38 trigger device
40 trigger device
42 time-amplitude-converter
44 histogramming device
46 analysis module
48 processor
50 storage for empirical data
52 storage for modelling software
54 output device
56 apparatus for elevating characteristics of target molecules
58 photo sensor
60 current amplifier
62 oscilloscope

What is claimed is:
1. An apparatus for evaluating one or more characteristics of target molecules, said apparatus comprising:
a biochip, said biochip comprising a substrate to which probe molecules are attached with a first portion thereof, said probe molecules being charged and having a fluorescence marker for allowing to generate fluorescence signals indicative of the distance of a second portion of said probe molecule from said substrate, said probe molecule being adapted to bind said target molecule,
means for generating and applying an external electric field which said probe molecules are exposed to, said field generation and applying means comprising a wave form generator suitable for generating a square wave signal switching between a first and a second polarity,
detecting means for detecting said fluorescence signal generated with said marker, said detecting means comprising:
a microscope for receiving fluorescence light from the fluorescence marker,
a single photon detector, coupled with said microscope, configured for micro-second time scale detection of single photons emitted from a fluorescence marker,
a first trigger coupled with the single photon detector, a second trigger operatively coupled with said waveform generator, and a time-to-amplitude converter coupled with both, the first and second trigger, wherein said first trigger is configured to input a first signal to the time-to-amplitude converter at the time that the external electrical field switches its polarity, said second trigger is configured to input a second signal to the time-to-amplitude converter in response to a single photon being detected by said single photon detector, and wherein the time-to-amplitude detector is configured to output a voltage signal representing a time value corresponding to a time difference between said first and second signals, and
a histogramming circuit coupled to an output of said time-to-amplitude converter, said histogramming circuit configured for increasing, in response to receiving said time value, a count in a histogram time bin corresponding to said received time value, thereby generating a histogram representing a time-resolved fluorescence measurement,
wherein the external electric field generated by said waveform generator causes:
(A) the second portion of the probe molecule to approach said substrate, and
(B) the second portion of the probe molecule to move away from said substrate,
while said signal detecting means detect single photons and update said time histogram to record said fluorescence signal indicative of said distance from said substrate as a function of time during at least one of steps (A) and step (B),
and wherein the electric field generation and applying means and the detecting means are configured to repeat steps (A) and (B) for a predetermined number of times and to combine the recorded signals by updating said histogram such as to generate an averaged time-resolved signal indicative of the process of said second part of said probe molecule approaching said substrate and/or moving away from said substrate, said apparatus further comprising an analysis module comprising a processor, said analysis module configured for analyzing and/or processing said combined signal such as to determine said one or more characteristics of said target molecule, and an output device or an interface for directly or indirectly coupling an output device for outputting the at least one or more characteristics of said target molecule.

2. The apparatus of claim 1, wherein said analysis module is configured to analyse and/or process said combined signal to:

determine a time delay between switching the external field between steps (A) and (B) and the time dependent signal reaching a predetermined threshold value, wherein said predetermined threshold value preferably corresponds to a predetermined percentage of the maximum of the combined value, and/or determine the time-derivative of the combined signal, and/or compare the combined signal with empirical data or model data obtained from an analytical model.

3. The apparatus according to claim 2, wherein said analytical model yields a probability distribution $p(\vec{x}, t)$ defining a probability that the probe molecule acquires a configuration $\vec{x}$ at a time t in a time dependent external field, and the size and/or Stokes radius of a target molecule is accounted for in said analytical model by a drift and/or a diffusion of the probability with regard to $\vec{x}$.

4. The apparatus according to claim 3, wherein said analysis module is configured to determine a diffusion coefficient or a drift coefficient by fitting a solution for $p(\vec{x}, t)$ of a Fokker-Planck equation containing said drift and/or diffusion coefficient with said combined time resolved signal, and configured to derive the size and/or Stokes radius of the target molecule from said determined drift and/or diffusion coefficient.

5. The apparatus according to claim 3, wherein the configuration is parameterized by an angle α of the probe molecule with regard to the substrate, and said diffusion coefficient is a rotational diffusion coefficient.

6. The apparatus of claim 1, wherein said analysis module is configured to evaluate one or more of the following target molecule characteristics:

effective Stokes radius, size, molecular weight,
the shape of the target molecule, in particular folding state and/or a deviation from a globular structure,
addition of further molecules to said target molecule, and
the charge of the target molecule.

7. The apparatus of claim 1, wherein said analysis module is configured to determine temperature changes or a change in the chemical environment of a fluid environment of the probe molecules.

8. The apparatus of claim 1, wherein said analysis module is configured to determine the effect of temperature changes or changes in the chemical environment on the target molecule.

9. The apparatus according to claim 1, wherein the first and/or second polarity has a period chosen long enough such that the probe molecules can acquire the respective states of maximum and minimum distance between said second portion and said substrate.

10. The apparatus according to claim 1, wherein the means for generating and applying an external electric field is configured to repeat steps (A) and (B) at least 10 times for a combined signal.

11. The apparatus according to claim 1, wherein said detector comprises a ramp-generator operatively coupled with said means for generating and applying an external electric field, and configured to receive the switching of the electric field between steps (A) and (B) as a first trigger signal causing the ramp-generator to start building up a voltage and operatively coupled with said single photon detector such as to receive the detection of a photon as a second trigger stopping the voltage build up, said built up voltage being at least approximately proportional to the time delay between the two triggers.

12. The apparatus according to claim 1, further configured to determine a forward rate ($k_{on}$) of the target molecule binding to the probe molecule and/or a backward rate ($k_{off}$) of the target molecule leaving the probe molecule by observing how the maximum of the time derivative of the combined signal changes in time after the probe molecules are exposed to said target molecules or after the exposure of said probe molecules to target molecules is terminated, respectively.

13. The apparatus according to claim 1, further configured to determine the charge of said target molecule based on a measurement and an analysis of the dependency of said signal indicative of the distance of said second portion of the probe molecule from said substrate on a static external field.

14. The apparatus according to claim 1, further configured to determine one or more of the following:

the presence of a certain target molecule in a sample,
the concentration of a target molecule in a sample,
the fraction of probe molecules occupied by a given target molecule, or
the stoichiometric ratio
of different target molecules that can bind to the same probe molecule capture part or
of the same target molecules in different configurations,
by carrying out the following steps:

(A) exposing said sample to a biochip, said biochip comprising a substrate to which probe molecules are attached with a first portion thereof, said probe molecules being charged and having a marker for allowing to generate signals indicative of the distance of a second portion of said probe molecule from said substrate, said probe molecule comprising a capture part capable of binding said target molecule or each of said target molecules of said group of target molecules, (B) applying an external electric field causing the second portion of the probe molecule to approach said substrate, (C) applying an external field causing the second portion of the probe molecule to move away from said substrate, wherein during step (A) and/or step (B) said signal indicative of said distance of said second portion from said substrate is recorded as a function of time, (D) repeating steps (A) and (B) for a predetermined number of times and combining the recorded signals such as to generate an averaged time-resolved signal indicative of the process of said second part of said probe molecule approaching said substrate and/or moving away from said substrate, and (E) carrying out one of the following steps:
identifying the presence of a certain target molecule by comparing said combined signal with a predetermined signal for said target, or
determining coefficients of a superposition of predetermined signals corresponding to the target-free probe molecule or the probe molecule with a respective target molecule bound thereto that fits the combined signal.

\* \* \* \* \*

UNITED STATES PATENT AND TRADEMARK OFFICE
CERTIFICATE OF CORRECTION

PATENT NO. : 9,885,687 B2
APPLICATION NO. : 14/856852
DATED : February 6, 2018
INVENTOR(S) : Ulrich Rant et al.

Page 1 of 1

It is certified that error appears in the above-identified patent and that said Letters Patent is hereby corrected as shown below:

In the Claims

In Column 27, Line 38 Claim 5:
Insert -- $\overline{x}$ -- after configuration

Signed and Sealed this
Seventeenth Day of April, 2018

Andrei Iancu
*Director of the United States Patent and Trademark Office*